US007294153B2

(12) United States Patent
Kleen et al.

(10) Patent No.: US 7,294,153 B2
(45) Date of Patent: Nov. 13, 2007

(54) CARING OXIDATION COLORING AGENT IN A TUBE

(75) Inventors: Astrid Kleen, Hamburg (DE); Mustafa Akram, Hamburg (DE); Stefan Hoepfner, Hamburg (DE); Hartmut Manneck, Klein Wesenberg (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 0 days.

(21) Appl. No.: 11/471,101

(22) Filed: Jun. 19, 2006

(65) Prior Publication Data
US 2006/0277695 A1    Dec. 14, 2006

Related U.S. Application Data

(63) Continuation of application No. PCT/EP2004/013932, filed on Dec. 8, 2004.

(30) Foreign Application Priority Data
Dec. 17, 2003 (DE) ................ 103 59 539

(51) Int. Cl.
*A61K 7/13* (2006.01)
(52) U.S. Cl. .................. 8/405; 8/425; 8/437; 8/451; 8/466; 8/552; 8/632; 8/646
(58) Field of Classification Search ............ 8/405, 8/425, 437, 451, 466, 552, 632, 646
See application file for complete search history.

(56) References Cited

U.S. PATENT DOCUMENTS

| 2,019,576 | A | 11/1935 | Makaelson |
| 3,753,968 | A | 8/1973 | Ward |
| 3,931,912 | A | 1/1976 | Hsiung |
| 4,184,844 | A | 1/1980 | Grollier et al. |
| 4,237,253 | A | 12/1980 | Jacquet et al. |
| 4,294,293 | A | 10/1981 | Lorenz et al. |
| 4,324,780 | A | 4/1982 | Jacquet et al. |
| 4,393,886 | A | 7/1983 | Strasilla et al. |
| 4,725,282 | A | 2/1988 | Hoch et al. |
| 4,814,101 | A | 3/1989 | Schieferstein et al. |
| 4,865,774 | A | 9/1989 | Fabry et al. |
| 4,931,218 | A | 6/1990 | Schenker et al. |
| 5,061,289 | A | 10/1991 | Clausen et al. |
| 5,136,093 | A | 8/1992 | Smith |
| 5,294,726 | A | 3/1994 | Behler et al. |
| 5,380,340 | A | 1/1995 | Neunhoeffer et al. |
| 5,480,459 | A | 1/1996 | Mager et al. |
| 5,534,267 | A | 7/1996 | Neunhoeffer et al. |
| 5,766,576 | A | 6/1998 | Lowe et al. |
| 5,773,595 | A | 6/1998 | Weuthen et al. |
| 6,099,592 | A | 8/2000 | Vidal et al. |
| 6,179,881 | B1* | 1/2001 | Henrion et al. ............... 8/407 |
| 6,284,003 | B1 | 9/2001 | Rose et al. |
| 6,485,528 | B1* | 11/2002 | Bartels et al. ............... 8/405 |
| 2002/0026675 | A1* | 3/2002 | Kravtchenko et al. ....... 8/405 |
| 2003/0106167 | A1 | 6/2003 | Rose |
| 2003/0150069 | A1 | 8/2003 | Kleen |
| 2003/0167578 | A1 | 9/2003 | Naumann |
| 2004/0049860 | A1 | 3/2004 | Cottard |

FOREIGN PATENT DOCUMENTS

| DE | 1 942 570 | 3/1970 |
| DE | 23 59 399 | 6/1975 |
| DE | 28 17 369 | 10/1978 |
| DE | 28 27 610 | 1/1980 |
| DE | 31 39 438 | 4/1983 |
| DE | 37 23 354 | 1/1989 |
| DE | 37 25 030 | 2/1989 |
| DE | 38 43 892 | 6/1990 |
| DE | 39 26 344 | 2/1991 |
| DE | 39 29 973 | 3/1991 |
| DE | 41 33 957 | 4/1993 |
| DE | 44 13 686 | 10/1995 |
| DE | 44 13 868 | 10/1995 |
| DE | 195 43 988 | 5/1997 |
| DE | 197 56 454 | 6/1999 |
| DE | 199 45 486 | 3/2001 |
| DE | 101 62 640 | 7/2003 |
| DE | 102 40 757 | 7/2003 |
| EP | 0 047 714 | 3/1982 |

(Continued)

OTHER PUBLICATIONS

Gutcho, M.H., ed., "Inorganic Pigments: Manufacturing Processes," Chemical Technology review No. 166, pp. 161-173, (1980) (ISBN: 0-8155-0811-5), no month.
Buxbaum, G., ed., "Industrial inorganic pigments, 2 edition", Weinheim, VCH, pp. 211-231 (1998), no month.
Zviak, C., ed., The Science of Hair Care, Chapter 7, pp. 248-250 vol. 7 "Dermatologie")(1986), no month.
Zviak, C., ed., The Science of Hair Care, Chapter 8 pp. 264-267, vol. 7 "Dermatologie")(1986), no month.

(Continued)

*Primary Examiner*—Eisa Elhilo
(74) *Attorney, Agent, or Firm*—John E. Drach

(57) ABSTRACT

Keratinic fibers are colored by a two-component composition for coloring keratinous fibers comprising a first preparation (A) comprising at least one oxidation dye precursor and a second preparation (B) comprising at least one care component, wherein the two preparations are packaged separately from one another in the compartments of a two-compartment tube.

The compartment openings in the tube are oriented in such a way that the contents of each of the chambers is emitted simultaneously into a common space.

19 Claims, No Drawings

FOREIGN PATENT DOCUMENTS

| | | |
|---|---|---|
| EP | 0 217 274 | 4/1987 |
| EP | 0 283 817 | 9/1988 |
| EP | 0 671 161 | 9/1995 |
| EP | 0 740 931 | 11/1996 |
| EP | 0 998 908 | 5/2000 |
| GB | 1 026 978 | 4/1966 |
| GB | 1 153 196 | 5/1969 |
| GB | 1 289 712 | 9/1972 |
| GB | 2 104 091 | 3/1983 |
| JP | 03-225052 | 10/1991 |
| WO | WO 86/00223 | 1/1986 |
| WO | WO 92/13829 | 8/1992 |
| WO | WO 93/23006 | 11/1993 |
| WO | WO 94/08969 | 4/1994 |
| WO | WO 94/08970 | 4/1994 |
| WO | WO 96/02162 | 2/1996 |
| WO | WO 96/15765 | 5/1996 |
| WO | WO 00/47714 | 8/2000 |
| WO | WO 01/97756 | 12/2001 |
| WO | WO 02/17274 | 2/2002 |
| WO | WO 02/45673 | 6/2002 |
| WO | WO 02/083817 | 10/2002 |
| WO | WO 03/089330 | 10/2003 |

OTHER PUBLICATIONS

Website printout, Enterprise and Industry, "Cosmetics—Introduction", from the European Commission, dated Jan. 23, 2006.

Schrader, K-H., "Grundlagen und Rezepturen der Kosmetika," 2nd edition, table of contents Huthig Verlag, Heidelberg, (1989), no month.

"International Cosmetic Ingredient Dictionary and Handbook," Seventh Ed., The Cosmetic, Toiletry and Fragrance Assn. Washington DC (1997), no month.

Guideline for declaring the contents of cosmetic agents, published by Assn. of Personal Hygiene and Washing Agents Industry (1996), no month.

U.S. Appl. No. 11/454,706, filed Jun. 15, 2006, Kleen.

U.S. Appl. No. 11/455,434, filed Jun. 19, 2006, Kleen.

* cited by examiner

CARING OXIDATION COLORING AGENT IN A TUBE

CROSS REFERENCE TO RELATED APPLICATIONS

This application is a continuation under 35 U.S.C. § 365(c) and 35 U.S.C. § 120 of International Application PCT/EP2004/013932, filed Dec. 8, 2004. This application also claims priority under 35 U.S.C. § 119 of DE 103 59 539.2, filed Dec. 17, 2003. Each application is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

This invention relates to a two-component composition for coloring keratinous fibers which is made up in a two-compartment tube, to a corresponding two-compartment tube and to a process for coloring keratinous fibers using this composition.

Nowadays, human hair is treated in many different ways with hair-care preparations. Such treatments include, for example, the cleaning of hair with shampoos, the care and regeneration of hair with rinses and treatments and the bleaching, coloring and shaping of hair with coloring and tinting formulations, wave formulations and styling preparations.

Coloring or tinting preparations containing substantive dyes as their coloring component are normally used for temporary colors. Substantive dyes are dye molecules which are directly absorbed onto the hair and do not require an oxidative process for forming the color. Such dyes include, for example, henna which has been used since olden times for coloring the body and the hair. They are generally far more sensitive to shampooing than oxidative colors, so that an often unwanted shift of tone or even visible "decoloring" occurs much more quickly.

So-called oxidation colorants are used for permanent, intensive colors with corresponding fastness properties. Oxidation colorants normally contain oxidation dye precursors, so-called primary intermediates and secondary intermediates. The primary intermediates form the actual dyes with one another or by coupling with one or more secondary intermediates under the influence of oxidizing agents or atmospheric oxygen. Oxidation colorants are distinguished by excellent, long-lasting coloring results. A mixture of a relatively large number of oxidation dye precursors normally has to be used for natural-looking colors. In many cases, substantive dyes are also used for shading.

The significance of care products with a long-lasting effect is growing due not least to the serious stressing of the hair by such color-changing treatments, but also to permanent waving, shampooing and harmful environmental factors. These care products influence the natural structure and properties of the hair. Thus, after treatment with a care product, the wet and dry combability of the hair, the hold, strength and volume of the hair can be optimized or the hair can be protected against high splitting rates.

Accordingly, it has long been common practice to subject the hair to a special aftertreatment in which the hair is treated with special active components, for example, quaternary ammonium salts or special polymers, usually in the form of a rinse. Depending on the formulation, the combability, hold and volume of the hair are improved and the splitting rate reduced by this treatment.

The active components available generally act preferentially on the surface of the hair. Thus, there are known active components which provide the hair with shine, hold, volume, better wet or dry combability or prevention of splitting. Just as important as the outward appearance of the hair, however, is the inner structural cohesion of the hair fibers, which can be seriously affected, in particular, by oxidative and reductive processes, such as coloring and permanent waving. Active components capable of permanently counteracting this change in the inner structure have also been proposed recently.

So-called combination preparations have recently been developed to reduce the complexity of the usual multistage processes, particularly where they are directly applied by the user. Besides the usual components for coloring the hair, these preparations also contain active components which previously had been reserved for the hair aftertreatment preparations. Accordingly, the consumer saves an application step. At the same time, packaging costs are reduced because one less product is used.

However, some of the known active components have the disadvantage that they cannot be stably formulated in the colorants.

(2) Description of Related Art

Including Information Disclosed Under 37 C.F.R. §§1.97 and 1.98.

Not Applicable

BRIEF SUMMARY OF THE INVENTION

It has now surprisingly been found that stable colorants with an excellent care effect can be obtained if a composition containing at least one oxidation dye precursor and a composition containing at least one care component are made up separately from one another in a two-compartment tube.

Accordingly, a first aspect of the present invention relates to two-component compositions for coloring keratinous fibers comprising a first preparation (A) containing at least one oxidation dye precursor and a second preparation (B) containing at least one care component, characterized in that the two preparations are made up separately from one another in the compartments of a two-compartment tube.

BRIEF DESCRIPTION OF THE SEVERAL VIEWS OF THE DRAWING(S)

Not Applicable

DETAILED DESCRIPTION OF THE INVENTION

The two-component compositions according to the invention are distinguished by an excellent care and coloring effect and by high stability. In addition, they ensure that the consumer applies the components in the mixing ratio proposed by the manufacturer. On the one hand, this increases product safety and, on the other hand, ensures that the product delivers the required performance.

In a first preferred embodiment, preparation (A) contains at least one primary intermediate. The primary intermediates normally used are primary aromatic amines with another free or substituted hydroxy or amino group in the para or ortho position, diaminopyridine derivatives, heterocyclic hydrazones, 4-aminopyrazole derivatives and 2,4,5,6-tetraminopyrimidine and derivatives thereof.

In a preferred embodiment of the invention, a p-phenylenediamine derivative or one of its physiologically compatible salts is used as the primary intermediate. Particular preference is attributed to p-phenylenediamine derivatives corresponding to formula (E1):

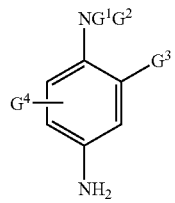

(E1)

in which
G$^1$ stands for a hydrogen atom, a C$_{1-4}$ alkyl radical, a C$_{1-4}$ monohydroxyalkyl radical, a C$_{2-4}$ polyhydroxyalkyl radical, a (C$_{1-4}$)-alkoxy-(C$_{1-4}$)-alkyl radical, a 4'-aminophenyl radical or a C$_{1-4}$ alkyl radical substituted by a nitrogen-containing group, a phenyl group or a 4'-aminophenyl group;
G$^2$ stands for a hydrogen atom, a C$_{1-4}$ alkyl radical, a C$_{1-4}$ monohydroxyalkyl radical, a C$_{2-4}$ polyhydroxyalkyl radical, a (C$_{1-4}$)-alkoxy-(C$_{1-4}$)-alkyl radical or a C$_{1-4}$ alkyl radical substituted by a nitrogen-containing group;
G$^3$ stands for a hydrogen atom, a halogen atom, such as a chlorine, bromine, iodine or fluorine atom, a C$_{1-4}$ alkyl radical, a C$_{1-4}$ monohydroxyalkyl radical, a C$_{2-4}$ polyhydroxyalkyl radical, a C$_{1-4}$ hydroxyalkoxy radical, a C$_{1-4}$ acetylaminoalkoxy radical, a C$_{1-4}$ mesylaminoalkoxy radical or a C$_{1-4}$ carbamoylaminoalkoxy radical;
G$^4$ is a hydrogen atom, a halogen atom or a C$_{1-4}$ alkyl radical or
if G$^3$ and G$^4$ are in the ortho position to one another, they may together form a bridging α,ω-alkylenedioxo group such as, for example, an ethylenedioxy group.

Examples of the C$_{1-4}$ alkyl groups mentioned as substituents in the compounds according to the invention are the methyl, ethyl, propyl, isopropyl and butyl groups. Ethyl and methyl groups are preferred alkyl groups. According to the invention, preferred C$_{1-4}$ alkoxy groups are, for example, methoxy or ethoxy groups. Other preferred examples of a C$_{1-4}$ hydroxyalkyl group are the hydroxymethyl, 2-hydroxyethyl, 3-hydroxypropyl or 4-hydroxybutyl group. A 2-hydroxyethyl group is particularly preferred. A particularly preferred C$_{2-4}$ polyhydroxyalkyl group is the 1,2-dihydroxyethyl group. According to the invention, examples of halogen atoms are F, Cl or Br atoms. Cl atoms are most particularly preferred. According to the invention, the other terms used are derived from the definitions given here. Examples of nitrogen-containing groups corresponding to formula (E1) are, in particular, the amino groups, C$_{1-4}$ monoalkylamino groups, C$_{1-4}$ dialkylamino groups, C$_{1-4}$ trialkylammonium groups, C$_{1-4}$ monohydroxyalkylamino groups, imidazolinium and ammonium.

Particularly preferred p-phenylenediamines corresponding to formula (E1) are selected from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(β-hydroxyethyl)-p-phenylenediamine, 4-N,N-bis-(β-hydroxyethyl)-amino-2-methylaniline, 4-N,N-bis-(β-hydroxyethyl)-amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl-β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane and physiologically compatible salts thereof.

According to the invention, most particularly preferred p-phenylenediamine derivatives of formula (E1) are p-phenylenediamine, p-toluylenediamine, 2-(β-hydroxyethyl)-p-phenylenediamine, 2-(α,β-dihydroxyethyl)-p-phenylenediamine and N,N-bis-(β-hydroxyethyl)-p-phenylenediamine.

In another preferred embodiment of the invention, compounds containing at least two aromatic nuclei substituted by amino and/or hydroxyl groups are used as primary intermediates.

The binuclear primary intermediates which may be used in the coloring compositions according to the invention include in particular compounds corresponding to formula (E2) and physiologically compatible salts thereof:

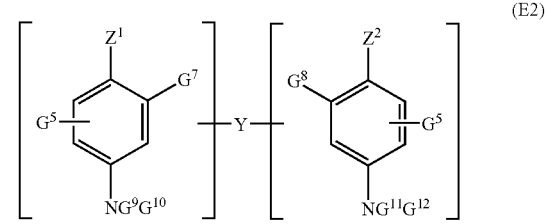

(E2)

in which
Z$^1$ and Z$^2$ independently of one another stand for a hydroxyl or NH$_2$ group which is optionally substituted by a C$_{1-4}$ alkyl group, by a C$_{1-4}$ hydroxyalkyl group and/or by a bridging group Y or which is optionally part of a bridging ring system,
the bridging group Y is a C$_{1-14}$ alkylene group such as, for example, a linear or branched alkylene chain or an alkylene ring which may be interrupted or terminated by one or more nitrogen-containing groups and/or one or more hetero atoms, such as oxygen, sulfur or nitrogen atoms, and may optionally be substituted by one or more hydroxyl or C$_{1-8}$ alkoxy groups or a direct bond,
G$^5$ and G$^6$ independently of one another stand for a hydrogen or halogen atom, a C$_{1-4}$ alkyl group, a C$_{1-4}$ monohydroxyalkyl group, a $C_{2-4}$ polyhydroxyalkyl group, a $C_{1-4}$ aminoalkyl group or a direct bond to the bridging group Y, $G^7$, $G^8$, $G^9$, $G^{10}$, $G^{11}$ and $G^{12}$ independently of one another stand for a hydrogen atom, a direct bond to the bridging group Y or a $C_{1-4}$ alkyl group, provided that the compounds of formula (E2) contain only one bridging group Y per molecule and the compounds of formula (E2) contain at least one amino group bearing at least one hydrogen atom.

According to the invention, the substituents used in formula (E2) are as defined in the foregoing.

Preferred binuclear primary intermediates corresponding to formula (E2) are, in particular, N,N'-bis-(β-hydroxyethyl)-N,N'-bis-(4'-aminophenyl)-1,3-diaminopropan-2-ol, N,N'-bis-(β-hydroxyethyl)-N,N'-bis-(4'-aminophenyl)-ethylenediamine, N,N'-bis-(4-aminophenyl)-tetramethylenediamine, N,N'-bis-(β-hydroxyethyl)-N,N'-bis-(4-aminophenyl)-tetramethylenediamine, N,N'-bis-(4-methylaminophenyl)-tetramethylenediamine, N,N'-diethyl-N,N'-bis-(4'-amino-3'-methylphenyl)-ethylenediamine, bis-(2-hydroxy-5-aminophenyl)-methane, 1,3-bis-(2,5-diaminophenoxy)-propan-2-ol, N,N'-bis-(4'-aminophenyl)-1,4-diaza-cycloheptane, N,N'-bis-(2-hydroxy-5-aminobenzyl)-piperazine, N-(4'-aminophenyl)-p-phenylenediamine and 1,10-bis-(2',5'-diaminophenyl)-1,4,7,10-tetraoxadecane and physiologically compatible salts thereof.

Particularly preferred binuclear primary intermediates of formula (E2) are N,N'-bis-(β-hydroxyethyl)-N,N'-bis-(4'-aminophenyl)-1,3-diaminopropan-2-ol, bis-(2-hydroxy-5-aminophenyl)-methane, 1,3-bis-(2,5-diaminophenoxy)-propan-2-ol, N,N'-bis-(4'-aminophenyl)-1,4-diazacycloheptane and 1,10-bis-(2',5'-diaminophenyl)-1,4,7,10-tetraoxadecane or a physiologically compatible salt thereof.

Bis-(2-hydroxy-5-aminophenyl)-methane is a most particularly preferred binuclear primary intermediate corresponding to formula (E2).

In another preferred embodiment of the invention, a p-aminophenol derivative or a physiologically compatible salt thereof is used as the primary intermediate. Particularly preferred p-aminophenol derivatives correspond to formula (E3):

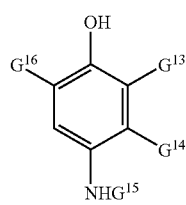

(E3)

in which $G^{13}$ stands for a hydrogen atom, a halogen atom, a $C_{1-4}$ alkyl group, a $C_{1-4}$ monohydroxyalkyl group, a $C_{2-4}$ polyhydroxyalkyl group, a $(C_{1-4})$-alkoxy-$(C_{1-4})$-alkyl group, a $C_{1-4}$ aminoalkyl group, a hydroxy-$(C_{1-4})$-alkylamino group, a $C_{1-4}$ hydroxyalkoxy group, a $C_{1-4}$ hydroxyalkyl-$(C_{1-4})$-aminoalkyl group or a (di-$C_{1-4}$-alkylamino)-$(C_{1-4})$-alkyl group, $G^{14}$ stands for a hydrogen atom or a halogen atom, a $C_{1-4}$ alkyl group, a $C_{1-4}$ monohydroxyalkyl group, a $C_{2-4}$ polyhydroxyalkyl group, a $(C_{1-4})$-alkoxy-$(C_{1-4})$-alkyl group, a $C_{1-4}$ aminoalkyl group or a $C_{1-4}$ cyanoalkyl group, $G^{15}$ stands for hydrogen, a $C_{1-4}$ alkyl group, a $C_{1-4}$ monohydroxyalkyl group, a $C_{2-4}$ polyhydroxyalkyl group, a phenyl group or a benzyl group and $G^{16}$ stands for hydrogen or a halogen atom.

According to the invention, the substituents used in formula (E3) are defined as in the foregoing.

Preferred p-aminophenols corresponding to formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)-phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)-phenol, 4-amino-2-(α,β-dihydroxyethyl)-phenol, 4-amino-2-fluorophenol, 4-amino-2-chlorophenol, 4-amino-2,6-dichlorophenol, 4-amino-2-(diethylaminomethyl)-phenol and physiologically compatible salts thereof.

Most particularly preferred compounds corresponding to formula (E3) are p-aminophenol, 4-amino-3-methylphenol, 4-amino-2-aminomethylphenol, 4-amino-2-(α,β-dihydroxyethyl)-phenol and 4-amino-2-(diethylaminomethyl)-phenol.

In addition, the primary intermediate may be selected from o-aminophenol and its derivatives such as, for example, 2-amino-4-methylphenol, 2-amino-5-methylphenol or 2-amino-4-chlorophenol.

The primary intermediate may also be selected from heterocyclic primary intermediates such as, for example, pyridine, pyrimidine, pyrazole, pyrazole-pyrimidine derivatives and physiologically compatible salts thereof.

Preferred pyridine derivatives are, in particular, the compounds described in GB 1,026,978 and GB 1,153,196, such as 2,5-diaminopyridine, 2-(4'-methoxyphenyl)-amino-3-aminopyridine, 2,3-diamino-6-methoxypyridine, 2-(β-methoxyethyl)-amino-3-amino-6-methoxypyridine and 3,4-diaminopyridine.

Preferred pyrimidine derivatives are, in particular, the compounds described in DE 2359399, JP 02019576 A2 and WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds described in patents DE 3843892 and DE 4133957 and in patent applications WO 94/08969, WO 94/08970, EP 740931 and DE 19543988, such as 4,5-diamino-1-methylpyrazole, 4,5-diamino-1-(β-hydroxyethyl)-pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert.butyl-1-methylpyrazole, 4,5-diamino-1-tert.butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)-amino-1,3-dimethylpyrazole, 3,4,5-triaminopyrazole, 1-methyl-3,4,5- triaminopyrazole, 3,5-diamino-1-methyl-4-methylaminopyrazole and 3,5-diamino-4-(β-hydroxyethyl)-amino-1-methylpyrazole.

Preferred pyrazole-pyrimidine derivatives are, in particular, the derivatives of pyrazole-[1,5-a]-pyrimidine corresponding to formula (E4) below and tautomeric forms thereof where a tautomeric equilibrium exists:

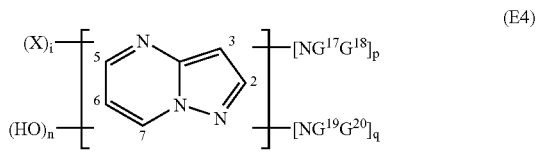

(E4)

in which

G$^{17}$, G$^{18}$, G$^{19}$ and G$^{20}$ independently of one another stand for a hydrogen atom, a C$_{1-4}$alkyl group, an aryl group, a C$_{1-4}$ hydroxyalkyl group, a C$_{2-4}$ polyhydroxyalkyl group a (C$_{1-4}$)-alkoxy-(C$_{1-4}$)-alkyl group, a C$_{1-4}$ aminoalkyl group which may optionally be protected by an acetylureide or sulfonyl group, a (C$_{1-4}$)-alkylamino-(C$_{1-4}$)-alkyl group, a di[(C$_{1-4}$)-alkyl]-(C$_{1-4}$)-aminoalkyl group, the dialkyl groups optionally forming a carbon cycle or a heterocycle with 5 or 6 links, a C$_{1-4}$ hydroxyalkyl or a di-(C$_{1-4}$)-[hydroxyalkyl]-(C$_{1-4}$)-aminoalkyl group;

the X's independently of one another stand for a hydrogen atom, a C$_{1-4}$ alkyl group, an aryl group, a C$_{1-4}$ hydroxyalkyl group, a C$_{2-4}$ polyhydroxyalkyl group, a C$_{1-4}$ aminoalkyl group, a (C$_{1-4}$)-alkylamino-(C$_{1-4}$)-alkyl group, a di[(C$_{1-4}$)-alkyl]-(C$_{1-4}$)-aminoalkyl group, the dialkyl groups optionally forming a carbon cycle or a heterocycle with 5 or 6 links, a C$_{1-4}$ hydroxyalkyl or a di-(C$_{1-4}$)-[hydroxyalkyl]-(C$_{1-4}$)-aminoalkyl group, an amino group, a C$_{1-4}$ alkyl or a di-(C$_{1-4}$ hydroxyalkyl)-amino group, a halogen atom, a carboxylic acid group or a sulfonic acid group, i has the value 0, 1, 2 or 3, p has the value 0 or 1, q has the value 0 or 1 and n has the value 0 or 1, provided that the sum of p+q is not 0, where p+q=2, n has the value 0 and the groups NG$^{17}$G$^{18}$ and NG$^{19}$G$^{20}$ occupy the (2,3); (5,6); (6,7); (3,5) or (3,7) positions;

where p+q=1, n has the value 1 and the groups NG$^{17}$G$^{18}$ (or NG$^{19}$G$^{20}$) and the group OH occupy the (2,3); (5,6); (6,7); (3,5) or (3,7) positions.

According to the invention, the substituents used in formula (E4) are as defined in the foregoing.

If the pyrazole-[1,5-a]-pyrimidine corresponding to formula (E4) above contains a hydroxy group in one of the positions 2, 5 or 7 of the ring system, a tautomeric equilibrium exists as illustrated, for example, in the following scheme:

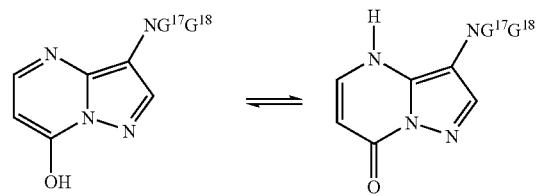

Among the pyrazole-[1,5-a]-pyrimidines corresponding to formula (E4) above, the following may be particularly mentioned:

pyrazole-[1,5-a]-pyrimidine-3,7-diamine;
2,5-dimethylpyrazole-[1,5-a]-pyrimidine-3,7-diamine;
pyrazole-[1,5-a]-pyrimidine-3,5-diamine;
2,7-dimethylpyrazole-[1,5-a]-pyrimidine-3,5-diamine;
3-aminopyrazole-[1,5-a]-pyrimidin-7-ol;
3-aminopyrazole-[1,5-a]-pyrimidin-5-ol;
2-(3-aminopyrazole-[1,5-a]-pyrimidin-7-ylamino)-ethanol;
2-(7-aminopyrazole-[1,5-a]-pyrimidin-3-ylamino)-ethanol;
2-[(3-aminopyrazole-[1,5-a]-pyrimidin-7-yl)-(2-hydroxyethyl)-amino]-ethanol;
2-[(7-aminopyrazole-[1,5-a]-pyrimidin-3-yl)-(2-hydroxyethyl)-amino]-ethanol;
5,6-dimethylpyrazole-[1,5-a]-pyrimidine-3,7-diamine;
2,6-dimethylpyrazole-[1,5-a]-pyrimidine-3,7-diamine;
3-amino-7-dimethylamino-2,5-dimethylpyrazole-[1,5-a]-pyrimidine;

and physiologically compatible salts thereof and tautomeric forms thereof where a tautomeric equilibrium exists.

The pyrazole-[1,5-a]-pyrimidines corresponding to formula (E4) above may be prepared by cyclization from an aminopyrazole or from hydrazine, as described in the literature.

In another preferred embodiment of the two-component composition according to the invention, the preparation (A) contains at least one secondary intermediate.

m-Phenylenediamine derivatives, naphthols, resorcinol and resorcinol derivatives, pyrazolones and m-aminophenol derivatives are generally used as secondary intermediates. Particularly suitable secondary intermediates are 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2', 4'-diaminophenoxy)-propane, 2-chlororesorcinol, 4-chlororesorcinol, 2-chloro-6-methyl-3-aminophenol, 2-amino-3-hydroxypyridine, 2-methyl resorcinol, 5-methyl resorcinol and 2-methyl-4-chloro-5-aminophenol.

According to the invention, preferred secondary intermediates are m-aminophenol and derivatives thereof, such as, for example, 5-amino-2-methylphenol, N-cycloperityl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-(diethylamino)-phenol, N-cyclopentyl-3-aminophenol, 1,3-dihydroxy-5-(methylamino)-benzene, 3-ethylamino-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis-(2',4'-diaminophenoxy)-propane, 1-methoxy-2-amino-4-(2'-hydroxyethylamino)benzene, 1,3-bis-(2',4'-diaminophenyl)-propane, 2,6-bis-(2'-hydroxyethylamino)-1-methylbenzene and 1-amino-3-bis-(2'-hydroxyethyl)-aminobenzene, o-diaminobenzene and derivatives thereof, such as, for example, 3,4-diaminobenzoic acid and 2,3-diamino-1-methylbenzene, di- or trihydroxybenzene derivatives, such as, for example, resorcinol, resorcinol monomethylether, 2-methylresorcinol, 5-methylresorcinol, 2,5-dimethylresorcinol, 2-chlororesorcinol, 4-chlororesorcinol, pyrogallol and 1,2,4-trihydroxybenzene, pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, morpholine derivatives, such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as 1-phenyl-3-methylpyrazol-5-one, for example, indole derivatives, such as, for example, 4-hydroxyindole, 6-hydroxyindole and 7-hydroxyindole, pyrimidine derivatives, such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine, or methylenedioxybenzene derivatives, such as, for example, 1-hydroxy-3,4-methylenedioxybenzene, 1-amino-3,4-methylenedioxybenzene and 1-(2'-hydroxyethyl)-amino-3,4-methylenedioxybenzene.

According to the invention, particularly preferred secondary intermediates are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

In a particularly preferred embodiment of the present invention, the preparation (A) contains at least one primary intermediate selected from p-phenylenediamine, p-toluylenediamine, p-aminophenol, N,N-bis-(2-hydroxyethyl)-p-phenylenediamine, 1-(2-hydroxyethyl)-2,5-diaminobenzene, 3-methyl-4-aminophenol, bis-(2-hydroxy-5-aminophenyl)-methane, 2,4,5,6-tetraminopyrimidine and 1-(2-hydroxyethyl)-4,5-diaminopyrazole and/or at least one other secondary intermediate selected from 2-(2,4-diaminophenoxy)-ethanol, 1,3-bis-(2,4-diaminophenoxy)-propane, 5-amino-2-methylphenol, 2-amino-3-hydroxypyridine, resorcinol, 2-methylresorcinol, 4-chlororesorcinol, 2-amino-4-(2-hydroxyethylamino)-anisole, 2,7-dihydroxynapthalene and 3-aminophenol.

The primary and secondary intermediates are present in preparation (A) in a quantity of preferably 0.005 to 20% by weight and more particularly 0.1 to 5% by weight, based on the two-component composition as a whole. The primary intermediates and secondary intermediates are generally used in a substantially equimolar ratio to one another. Although it has proven to be advantageous to use the primary and secondary intermediates in an equimolar ratio, there is no disadvantage in using individual oxidation dye precursors in a certain excess, so that primary intermediates and secondary intermediates may be present in a molar ratio of 1:0.5 to 1:3 and, more particularly, 1:1 to 1:2.

In another embodiment of the present invention, preparation (A) may contain a precursor of a "nature-analogous" dye. Preferred precursors of "nature-analogous" dyes are indoles and indolines which contain at least one hydroxy or amino group, preferably as a substituent on the six ring. These groups may carry further substituents, for example, in the form of an etherification or esterification of the hydroxy group or an alkylation of the amino group. In a second preferred embodiment, the colorants contain at least one indole and/or indoline derivative.

Particularly suitable precursors of "nature-analogous" hair dyes are derivatives of 5,6-dihydroxyindoline corresponding to formula (Ia):

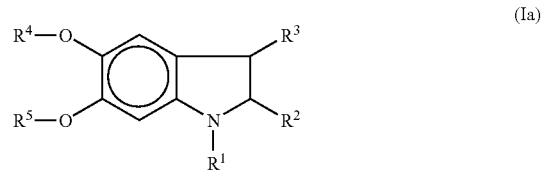

in which—independently of one another—

R$^1$ is hydrogen, a C$_{1-4}$ alkyl group or a C$_{1-4}$ hydroxyalkyl group,

R$^2$ is hydrogen or a —COOH group, the —COOH group optionally being present as a salt with a physiologically compatible cation, R$^3$ is hydrogen or a C$_{1-4}$ alkyl group, R$^4$ is hydrogen, a C$_{1-4}$ alkyl group or a group —CO—R$^6$, where R$^6$ is a C$_{1-4}$ alkyl group, and R$^5$ is one of the groups mentioned for R$^4$, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, particular emphasis is placed on N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

Other particularly suitable precursors of "nature-analogous" hair dyes are derivatives of 5,6-dihydroxyindole corresponding to formula (IIb):

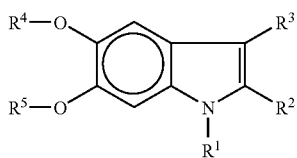

in which—independently of one another—

R¹ is hydrogen, a $C_{1-4}$ alkyl group or a $C_{1-4}$ hydroxyalkyl group,

R² is hydrogen or a —COOH group, the —COOH group optionally being present as a salt with a physiologically compatible cation, R³ is hydrogen or a $C_{1-4}$ alkyl group, R⁴ is hydrogen, a $C_{1-4}$ alkyl group or a group —CO—R⁶, where R⁶ is a $C_{1-4}$ alkyl group, and R⁵ is one of the groups mentioned for R⁴, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, particular emphasis is placed on N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives may be used both as free bases and in the form of their physiologically compatible salts with inorganic or organic acids, for example, hydrochlorides, sulfates and hydrobromides, in the two-component compositions according to the invention. The indole or indoline derivatives are present in these compositions in quantities of normally 0.05 to 10% by weight and preferably 0.2 to 5% by weight, based on the two-component composition as a whole.

In another preferred embodiment of the invention, the indoline or indole derivative may be used in combination with at least one amino acid or an oligopeptide in hair colorants. The amino acid is advantageously an α-amino acid. Most particularly preferred α-amino acids are arginine, ornithine, lysine, serine and histidine, especially arginine.

According to the invention, preparation (A) may contain one or more substantive dyes besides the primary and/or secondary intermediates for the purpose of shading. Substantive dyes are typically nitrophenylenediamines, nitroaminophenols, azo dyes, anthraquinones or indophenols. Preferred substantive dyes are the compounds known under the International names or commercial names of HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1 and Acid Black 52 and also 1,4-diamino-2-nitrobenzene, 2-amino-4-nitrophenol, 1,4-bis-(β-hydroxyethyl)-amino-2-nitrobenzene, 3-nitro-4-(β-hydroxyethyl)-aminophenol, 2-(2'-hydroxyethyl)-amino-4,6-dinitrophenol, 1-(2'-hydroxyethyl)-amino-4-methyl-2-nitrobenzene, 1-amino-4-(2'-hydroxyethyl)-amino-5-chloro-2-nitrobenzene, 4-amino-3-nitrophenol, 1-(2'-ureidoethyl)-amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

In a preferred embodiment of the present invention, preparation (A) contains a cationic substantive dye. Particularly preferred are (a) cationic triphenylmethane dyes such as, for example, Basic Blue 7, Basic Blue 26, Basic Violet 2 and Basic Violet 14, (b) aromatic systems substituted by a quaternary nitrogen group such as, for example, Basic Yellow 57, Basic Red 76, Basic Blue 99, Basic Brown 16 and Basic Brown 17 and (c) substantive dyes containing a heterocycle with at least one quaternary nitrogen atom as disclosed, for example, in EP-A2 998 908, to which reference is specifically made at this juncture, in claims 6 to 11.

Preferred cationic substantive dyes of group (c) are, in particular, the following compounds:

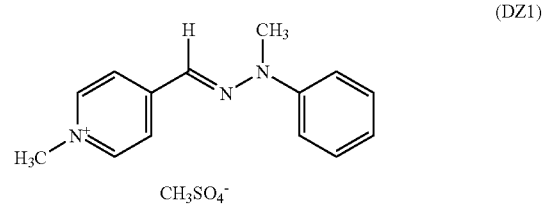

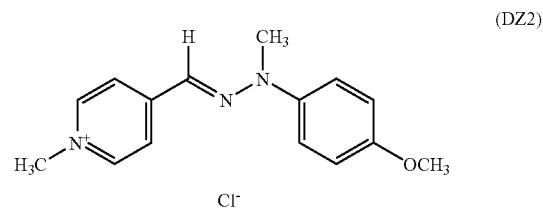

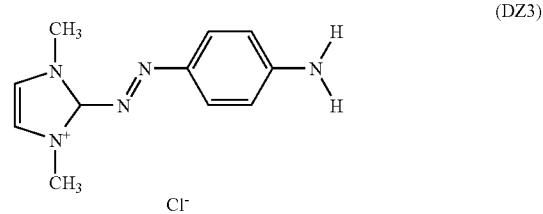

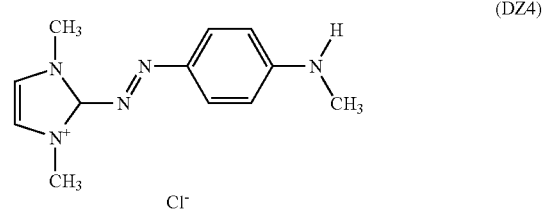

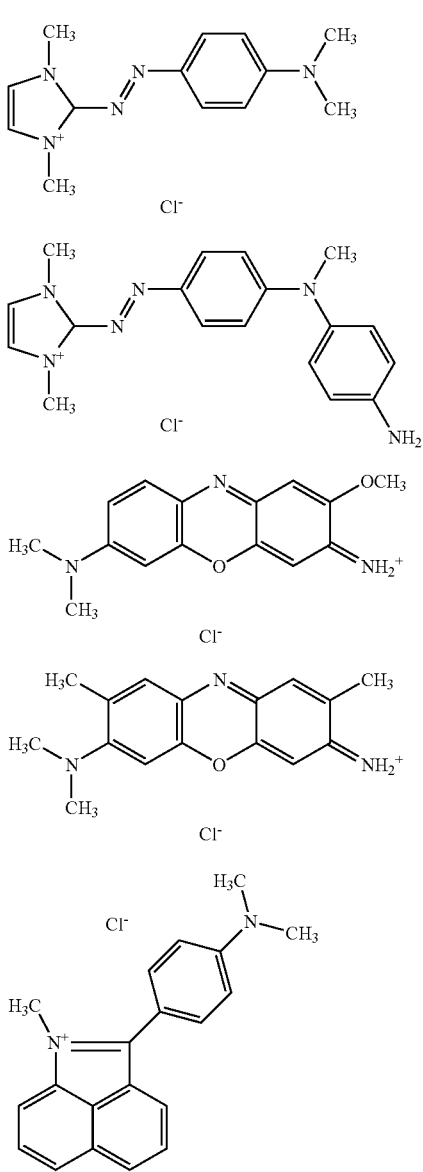

The compounds corresponding to formula (DZ1), (DZ3) and (DZ5), which are also known by the names of Basic Yellow 87, Basic Orange 31 and Basic Red 51, are most particularly preferred cationic substantive dyes of group (c).

According to the invention, the cationic substantive dyes marketed under the name of Arianor® are also particularly preferred cationic substantive dyes.

The compositions according to the invention of this embodiment contain the substantive dyes in a quantity of preferably 0.01 to 20% by weight, based on the two-component composition as a whole.

The compositions according to the invention may also contain naturally occurring dyes such as, for example, henna red, henna neutral, henna black, camomile blossom, sandalwood, black tea, black alder bark, sage, logwood, madder root, catechu, sedre and alkanet.

The oxidation dye precursors or the substantive dyes do not have to be single compounds. On the contrary, other components may be present in small quantities in the hair colorants according to the invention due to the processes used to produce the individual dyes providing these other components do not adversely affect the coloring result or have to be ruled out for other reasons, for example, toxicological reasons.

So far as the dyes suitable for use in the two-component compositions according to the invention are concerned, reference is also expressly made to the work by Ch. Zviak, The Science of Hair Care, Chapter 7 (pages 248-250; substantive dyes) and Chapter 8, pages 264-267; oxidation dye precursors), published as Volume 7 of the Series "Dermatology" (Ed.: Ch. Culnan and H. Maibach), Marcel Dekker Inc., New York/Basle, 1986, and to the "Europäische Inventar der Kosmetik-Rohstoffe" published by the Europäische Gemeinschaft and available in disk form from the Bundesverband Deutscher Industrie- und Handelsunternehmen für Arzneimittel, Reformwaren und Körperpflegemittel d.V., Mannheim.

The two-component compositions according to the invention additionally contain at least one care component as an essential constituent in preparation (B).

In a first preferred embodiment, the two-component composition according to the invention contains at least one cationic surfactant as the care component.

According to the invention, the cationic surfactants used are preferably those of the quaternary ammonium compound, esterquat and amidoamine type. Preferred quaternary ammonium compounds are ammonium halides, more particularly chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride and the imidazolium compounds known under the INCI names of Quaternium-27 and Quaternium-83. The long alkyl chains of the above-mentioned surfactants preferably contain 10 to 18 carbon atoms.

Esterquats are known substances which contain both at least one ester function and at least one quaternary ammonium group as structural element. Preferred esterquats are quaternized ester salts of fatty acids with triethanolamine, quaternized ester salts of fatty acids with diethanol alkylamines and quaternized ester salts of fatty acids with 1,2-dihydroxypropyl dialkylamines. Such products are marketed, for example, under the names of Stepantex®, Dehyquart® and Armocare®. The products Armocare® VGH-70, an N,N-bis-(2-palmitoyloxyethyl)-dimethyl ammonium chloride, and Dehyquart® F-75, Dehyquart® C-4046, Dehyquart® L80 and Dehyquart® AU-35 are examples of such esterquats.

The alkyl amidoamines are normally prepared by amidation of natural or synthetic fatty acids and fatty acid cuts with dialkyl aminoamines. A compound from this group particularly suitable for the purposes of the invention is the stearamidopropyl dimethylamine obtainable under the name of Tegoamid® S 18.

The cationic surfactants are present in the two-component compositions according to the invention in quantities of preferably 0.05 to 10% by weight, based on the preparation applied as a whole. Quantities of 0.1 to 5% by weight are particularly preferred.

In a second preferred embodiment of the present invention, the two-component composition contains at least one hair-care polymer as the care component.

A first group of the hair-care polymers are the cationic polymers. Cationic polymers in the context of the invention are polymers containing a group which may be "temporarily" or "permanently" cationic in the main chain and/or side chain. According to the invention, "permanently cationic polymers" are polymers which contain a cationic group irrespective of the pH of the preparation. These are generally polymers which contain a quaternary nitrogen atom, for example, in the form of an ammonium group. Preferred cationic groups are quaternary ammonium groups. Polymers where the quaternary ammonium group is attached by a $C_{1-4}$ hydrocarbon group to a polymer main chain made up of acrylic acid, methacrylic acid or derivatives thereof have proven to be particularly suitable.

Particularly preferred cationic polymers are homopolymers corresponding to general formula (G1-I):

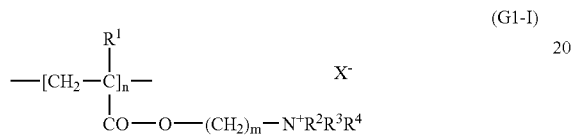

(G1-I)

in which $R^1$=—H or —$CH_3$, $R^2$, $R^3$ and $R^4$ independently of one another are selected from $C_{1-4}$ alkyl, alkenyl or hydroxyalkyl groups, m=1, 2, 3 or 4, n is a natural number and $X^-$ is a physiologically compatible organic or inorganic anion, and copolymers consisting essentially of the monomer units shown in formula (G1-I) and nonionic monomer units. Among these polymers, those to which at least one of the following conditions applies:

$R^1$ is a methyl group,
$R^2$, $R^3$ and $R^4$ are methyl groups,
m has the value 2, are particularly preferred for the purposes of the invention.

The physiologically compatible counterion $X^-$ may be selected, for example, from halide ions, sulfate ions, phosphate ions, methosulfate ions and organic ions, such as lactate, citrate, tartrate and acetate ions. Halide ions, especially chloride, are preferred.

A particularly suitable homopolymer is the optionally crosslinked poly(methacryloyloxyethyltrimethylammoniumchloride) with the INCI name Polyquaternium-37. Crosslinking may be carried out, if desired, with polyolefinically unsaturated compounds, for example, divinyl benzene, tetraallyl oxyethane, methylene bisacrylamide, diallyl ether, polyallyl polyglyceryl ether or allyl ethers of sugars or sugar derivatives, such as erythritol, pentaerythritol, arabitol, mannitol, sorbitol, sucrose or glucose. Methylene bisacrylamide is a preferred crosslinking agent.

The homopolymer is preferably used in the form of a nonaqueous polymer dispersion which should have a percentage polymer content of not less than 30% by weight. Such polymer dispersions are commercially available under the names of Salcare® SC 95 (ca. 50% polymer content, other components: mineral oil (INCI name: Mineral Oil) and tridecyl polyoxypropylene/polyoxyethylene ether (INCI name: PPG-1-Trideceth-6)) and Salcare® SC 96 (ca. 50% polymer content, other components: mixture of diesters of propylene glycol with a mixture of caprylic and capric acid (INCI name: Propylene Glycol Dicaprylate/Dicaprate) and tridecyl polyoxypropylene/polyoxyethylene ether (INCI name: PPG-1-Trideceth-6).

Copolymers containing monomer units corresponding to formula (G1-I) preferably contain acrylamide, methacrylamide, $C_{1-4}$ alkyl acrylate and $C^{1-4}$ alkyl methacrylate as nonionic monomer units. Of these nonionic monomers, acrylamide is particularly preferred. As in the case of the homopolymers described above, these copolymers may also be crosslinked. According to the invention, a preferred copolymer is the crosslinked acrylamide/methacryloyloxyethyl trimethyl ammonium chloride copolymer. Copolymers in which the monomers are present in a ratio by weight of about 20:80 are commercially available as a ca. 50% nonaqueous polymer dispersion with the name of Salcare® SC 92.

Other preferred cationic polymers are, for example:

the quaternized cellulose derivatives commercially available under the names of Celquat® and Polymer JR®. The compounds Celquat® H 100, Celquat® L 200 and Polymer JR® 400 are preferred quaternized cellulose derivatives, the cationic alkyl polyglycosides according to DE-PS 44 13 868, cationized honey, for example, the commercial product Honeyquat® 50, cationic guar derivatives such as, in particular, the products marketed under the names of Cosmedia® Guar and Jaguar®, polysiloxanes containing quaternary groups such as, for example, the commercially available products Q2-7224 (manufacturer: Dow Corning; a stabilized trimethyl silyl amodimethicone), Dow Corning® 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80), polymeric dimethyl diallyl ammonium salts and copolymers thereof with esters and amides of acrylic acid and methacrylic acid. The products commercially available under the names of Merquat® 100 (poly(dimethyl diallylammonium chloride)) and Merquat® 550 (dimethyl diallylammonium chloride/acrylamide copolymer) are examples of such cationic polymers, copolymers of vinyl pyrrolidone with quaternized derivatives of dialkylaminoacrylate and methacrylate such as, for example, vinyl pyrrolidone/dimethylaminoethyl methacrylate copolymers quaternized with diethyl sulfate. Such compounds are commercially available under the names of Gafquate 734 and Gafquate 755, the vinyl pyrrolidone/vinyl imidazolinium methochloride copolymers commercially available under the names of Luviquate FC 370, FC 550, FC 905 and HM 552, quaternized polyvinyl alcohol;

and the polymers containing quaternary nitrogen atoms in the main polymer chain known under the names of Polyquaternium 2, Polyquaternium 17, Polyquaternium 18 and Polyquaternium 27.

Other suitable cationic polymers are the polymers known by the names of Polyquaternium 24 (commercial product: Quatrisoft® LM 200, for example). Also suitable for use in accordance with the invention are the vinyl pyrrolidone copolymers known by the commercial names of Copolymer 845 (manufacturer: ISP), Gaffixe VC 713 (manufacturer: ISP), Gafquat® ASCP 1011, Gafquat®HS 110, Luviquat® 8155 and Luviquat® MS 370.

Other cationic polymers according to the invention are the so-called "temporarily cationic" polymers. These polymers typically contain an amino group which is present as a quaternary ammonium group, i.e. is cationic, at certain pH values. Preferred such polymers are, for example, chitosan and derivatives thereof which are freely available on the market, for example, under the names of Hydagen® CMF, Hydagen® HCMF, Kytamer® PC and Chitolam® NB/101.

Preferred cationic polymers according to the invention are cationic cellulose derivatives and chitosan and chitosan derivatives, more particularly, the commercial products Polymer® JR 400, Hydagen® HCMF and Kytamer® PC, cationic guar derivatives, cationic honey derivatives, more particularly the commercial product Honeyquat® 50, the cationic alkyl polyglycosides according to DE-PS 44 13 686 and polymers of the Polyquaternium-37 type.

The cationic polymers also include cationized protein hydrolyzates; the basic protein hydrolyzate can come from animals, for example, from collagen, milk or keratin, from plants, for example, from wheat, corn, rice, potatoes, soya or almonds, from marine organisms, for example, from fish collagen or algae, or biotechnologically produced protein hydrolyzates. The protein hydrolyzates on which the cationic derivatives according to the invention are based can be obtained from the corresponding proteins by chemical, more particularly alkaline or acidic, hydrolysis, by enzymatic hydrolysis and/or a combination of both forms of hydrolysis. The hydrolysis of proteins generally gives a protein hydrolyzate with a molecular weight distribution of ca. 100 dalton up to several thousand dalton. Preferred protein hydrolyzates are those of which the basic protein component has a molecular weight of 100 to 25,000 dalton and preferably 250 to 5,000 dalton. Cationic protein hydrolyzates are also understood to include quaternized amino acids and mixtures thereof. The quaternization of the protein hydrolyzates or the amino acids is frequently carried out with quaternary ammonium salts such as, for example, N,N-dimethyl-N-(n-alkyl)-N-(2-hydroxy-3-chloro-n-propyl)-ammonium halides. The cationic protein hydrolyzates may also be further derivatized. Typical examples of the cationic protein hydrolyzates and derivatives according to the invention are the commercially available products mentioned under their INCI names in the International Cosmetic Ingredient Dictionary and Handbook (7th Edition 1997, The Cosmetic, Toiletry and Fragrance Association, 1101 17th Street, N.W., Suite 300, Washington, D.C. 20036-4702): Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/ Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryidimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein.

Cationic protein hydrolyzates and derivatives from vegetable sources are most particularly preferred.

Other hair-care polymers suitable for use in accordance with the invention are the amphoteric compounds mentioned in GB-A-2 104 091, EP-A47 714, EP-A-217 274, EP-A-283 817 and DE-A 28 17 369.

Preferred amphoteric polymers are polymers essentially consisting of (a) monomers containing quaternary ammonium groups corresponding to general formula (II):

$$R^1\text{—}CH\text{=}CR^2\text{—}CO\text{-}Z\text{-}(C_nH_{2n})\text{—}N^{(+)}R^3R^4R^5A^{(-)} \quad (II)$$

in which $R^1$ and $R^2$ independently of one another represent hydrogen or a methyl group and $R^3$, $R^4$ and $R^5$ independently of one another represent alkyl groups containing 1 to 4 carbon atoms, Z is an NH group or an oxygen atom, n is an integer of 2 to 5 and $A^{(-)}$ is the anion of an organic or inorganic acid, and (b) monomeric carboxylic acids corresponding to general formula (III):

$$R^6\text{—}CH\text{=}CR^7\text{—}COOH \quad (III)$$

in which $R^6$ and $R^7$ independently of one another are hydrogen or methyl groups.

According to the invention, these compounds may be used both directly and in the salt form obtained by neutralization of the polymers, for example, with an alkali metal hydroxide. Particulars of the production of these polymers can be found in DE-A 39 29 973. Most particularly preferred polymers are those where type (a) monomers, in which $R^3$, $R^4$ and $R^5$ are methyl groups, Z is an NH group and $A^{(-)}$ is a halide, methoxysulfate or ethoxysulfate ion, are used; acrylamidopropyl trimethyl ammonium chloride is a particularly preferred monomer (a). Acrylic acid is preferably used as the monomer (b) for the polymers mentioned.

The two-component compositions according to the invention contain the cationic hair-care polymers in a quantity of preferably 0.01 to 5% by weight and more particularly 0.1 to 2% by weight, based on the preparation applied as a whole.

In a third preferred embodiment, the two-component compositions according to the invention contain at least one UV filter. There are no general restrictions on either the structure or the physical properties of the UV filters to be used in accordance with the invention. On the contrary, any cosmetically usable UV filters of which the absorption maximum lies in the UVA range (315-400 nm), the UVB range (280-315 nm) or the UVC range (<280 nm) may be used. UV filters with an absorption maximum in the UVB range, more particularly in the range from about 280 to about 300 nm, are particularly preferred.

The UV filters preferably used in accordance with the invention may be selected, for example, from substituted benzophenones, p-aminobenzoic acid esters, diphenyl acrylic acid esters, cinnamic acid esters, salicylic acid esters, benzimidazoles and o-aminobenzoic acid esters.

Examples of UV filters suitable for use in accordance with the invention are 4-aminobenzoic acid, N,N,N-trimethyl-4-(2-oxoborn-3-ylidenemethyl)-aniline methyl sulfate, 3,3,5-trimethyl cyclohexyl salicylate (Homosalate), 2-hydroxy-4-methoxybenzophenone (Benzophenone-3; Uvinul® M 40, Uvasorb® MET, Neo Heliopan® BB, Eusolex® 4360), 2-phenylbenzimidazole-5-sulfonic acid and potassium, sodium and triethanolamine salts thereof (Phenylbenzimidazole sulfonic acid; Parsole HS, Neo Heliopan® Hydro), 3,3'-(1,4-phenylenedimethylene)-bis-(7,7-dimethyl-2-oxo-bicyclo-[2.2.1]hept-1-yl methanesulfonic acid) and salts thereof, 1-(4-tert.-butylphenyl)-3-(4-methoxyphenyl)-propane-1,3-dione (Butyl methoxydibenzoylmethane; Parsol® 1789, Eusolex® 9020), α-(2-oxoborn-3-ylidene)-toluene-4-sulfonic acid and salts thereof, ethoxylated 4-aminobenzoic acid ethyl ester (PEG-25 PABA; Uvinul® P 25), 4-dimethylaminobenzoic acid-2-ethylhexyl ester (Octyl Dimethyl PABA; Uvasorb® DMO, Escalol® 507, Eusolex® 6007), salicylic acid-2-ethyl hexyl ester (Octyl Salicylate; Escalol® 587, Neo Heliopan® OS, Uvinul® 018), 4-methoxycinnamic acid isopentyl ester (Isoamyl p-Methoxycinnamate; Neo Heliopan® E 1000), 4-methoxycinnamic acid-2-ethylhexyl ester (Octyl Methoxycinnamate; Parsol® MCX, Escalol® 557, Neo Heliopan® AV), 2-hydroxy-4-methoxybenzophenone-5-sulfonic acid and its sodium salt (Benzophenone-4; Uvinul® MS 40; Uvasorb® S 5), 3-(4'-methylbenzylidene)-D,L-camphor (4-Methylbenzylidene camphor; Parsol® 5000, Eusolex® 6300), 3-benzylidene camphor (3-Benzylidene camphor), 4-isopropyl benzyl salicylate, 2,4,6-trianilino-(p-carbo-2'-ethylhexyl-1'-oxy)-1,3,5-triazine, 3-imidazol-4-yl acrylic acid and its ethyl ester, polymers of N-{(2 and 4)-[2-oxoborn-3-ylidenemethyl]benzyl}-acrylamide, 2,4-dihydroxybenzophenone (Benzophenone-1; Uvasorb® 20H, Uvinul® 400), 1,1'-diphenylacrylonitrile acid-2-ethylhexyl ester (Octocrylene; Eusolex® OCR, Neo Heliopan® Type 303, Uvinul® N 539 SG), o-aminobenzoic acid menthyl ester (Menthyl Anthranilate; Neo Heliopane MA), 2,2',4,4'-tetrahydroxybenzophenone (Benzophenone-2; Uvinul® D-50), 2,2'-dihydroxy-4,4'-dimethoxybenzophenone (Benzophenone-6), 2,2'-dihydroxy-4,4'-dimethoxybenzophenone-5-sodium sulfonate and 2-cyano-3,3-diphenylacrylic acid-2'-ethyl hexyl ester. Preferred UV filters are 4-aminobenzoic acid, N,N,N-trimethyl-4-(2-oxoborn-3-ylidenemethyl)-aniline methyl sulfate, 3,3,5-trimethyl cyclohexyl salicylate, 2-hydroxy-4-methoxybenzophenone, 2-phenylbenzimidazole-5-sulfonic acid and potassium, sodium and triethanolamine salts thereof, 3,3'-(1,4-phenylenedimethylene)-bis-(7,7-dimethyl-2-oxo-bicyclo-[2.2.1]hept-1-yl methanesulfonic acid) and salts thereof, 1-(4-tert.-butylphenyl)-3-(4-methoxyphenyl)-propane-1,3-dione, α-(2-oxoborn-3-ylidene)-toluene-4-sulfonic acid and salts thereof, ethoxylated 4-aminobenzoic acid ethyl ester, 4-dimethylaminobenzoic acid-2-ethylhexyl ester, salicylic acid-2-ethyl hexyl ester, 4-methoxycinnamic acid isopentyl ester, 4-methoxycinnamic acid-2-ethylhexyl ester, 2-hydroxy-4-methoxybenzophenone-5-sulfonic acid and its sodium salt, 3-(4'-methylbenzylidene)-D,L-camphor, 3-benzylidene camphor, 4-isopropyl benzyl salicylate, 2,4,6-trianilino-(p-carbo-2'-ethylhexyl-1'-oxy)-1,3,5-triazine, 3-imidazol-4-yl acrylic acid and its ethyl ester, polymers of N-{(2 and 4)-[2-oxoborn-3-ylidenemethyl]benzyl}-acrylamide. According to the invention, 2-hydroxy-4-methoxybenzophenone, 2-phenylbenzimidazole-5-sulfonic acid and potassium, sodium and triethanolamine salts thereof, 1-(4-tert.butylphenyl)-3-(4-methoxyphenyl)-propane-1,3-dione, 4-methoxycinnamic acid-2-ethylhexyl ester and 3-(4'-methylbenzylidene)-,D,L-camphor are most particularly preferred.

UV filters with a molar extinction coefficient at the absorption maximum of more than 15,000 and more particularly above 20,000 are preferred.

It has also been found that, with structurally similar UV filters, the water-insoluble compound in many cases is more effective in the context of the teaching according to the invention than water-soluble compounds which are distinguished from it by one or more additional ionic groups. In the context of the invention, water-insoluble UV filters are UV filters of which no more than 1% by weight and, more particularly, no more than 0.1% by weight dissolves in water at 20° C. In addition, at least 0.1% by weight and, more particularly, at least 1% by weight of these compounds should dissolve in typical cosmetic oil components at room temperature. Accordingly, it may be preferable in accordance with the invention to use water-insoluble UV filters.

In another embodiment of the invention, preferred UV filters contain a cationic group, more particularly, a quaternary ammonium group.

These UV filters have the general structure U-Q where the structural moiety U is a UV-absorbing group. In principle, this group may be derived from the known, cosmetically usable UV filters mentioned above in which one group, generally a hydrogen atom, of the UV filter is replaced by a cationic group Q, more particularly, with a quaternary amino function.

Examples of compounds from which the structural moiety U may be derived are
  substituted benzophenones,
  p-aminobenzoic acid esters,
  diphenylacrylic acid esters,
  cinnamic acid esters,
  salicylic acid esters,
  benzimidazoles and
  o-aminobenzoic acid esters.

According to the invention, preferred structural moieties U are derived from cinnamic acid amide or from N,N-dimethylaminobenzoic acid amide.

In principle, the structural moieties U may be selected so that the absorption maximum of the UV filters can lie both in the UVA (315-400 nm) range and in the UVB (280-315 nm) range or in the UVC (<280 nm) range. UV filters with an absorption maximum in the UVB range, more especially in the range from about 280 to about 300 nm, are particularly preferred.

In addition, the structural moiety U may preferably be selected—even in dependence upon the structural moiety Q—so that the molar extinction coefficient of the UV filter at the absorption maximum is above 15,000 and more particularly above 20,000.

The structural moiety Q preferably contains a quaternary ammonium group as the cationic group. In principle, this quaternary ammonium group may be directly attached to the structural moiety U so that the structural moiety U represents one of the four substituents of the positively charged nitrogen atom. However, one of the four substituents at the positively charged nitrogen atom is preferably a group, more particularly an alkylene group containing 2 to 6 carbon atoms, which acts as a link between the structural moiety U and the positively charged nitrogen atom.

The group Q advantageously has the general structure —$(CH_2)_xN^+ R^1R^2R^3 X^-$, where x is an integer of 1 to 4, $R^1$ and $R^2$ independently of one another represent $C_{1-4}$ alkyl groups, $R^3$ is a $C_{1-22}$ alkyl group or a benzyl group and $X^-$ is a physiologically compatible anion. In this general structure, x is preferably the number 3, $R^1$ and $R^2$ each represent a methyl group and $R^3$ is either a methyl group or a saturated or unsaturated, linear or branched hydrocarbon chain containing 8 to 22 and more particularly 10 to 18 carbon atoms.

Physiologically compatible anions are, for example, inorganic anions, such as halides, more particularly chloride, bromide and fluoride, sulfate ions and phosphate ions, and organic anions, such as lactate, citrate, acetate, tartrate, methosulfate and tosylate.

Two preferred UV filters containing cationic groups are the compounds obtainable as commercial products cinnamic acid amidopropyl trimethylammonium chloride (Incroqua® UV-283) and dodecyl dimethylaminobenzamidopropyl dimethylammonium tosylate (Escalol® HP 610).

The teaching according to the invention does of course also encompass the use of a combination of several UV filters. In this embodiment, a combination of at least one water-insoluble UV filter with at least one UV filter containing a cationic group is preferred. The UV filters (I) are present in the compositions according to the invention in quantities of normally 0.01 to 5% by weight and preferably 0.1 to 2.5% by weight, based on the preparation applied as a whole.

In a fourth preferred embodiment, the two-component compositions according to the invention contain at least one vitamin, provitamin, vitamin precursor and/or derivative thereof as the care component.

Vitamins, provitamins and vitamin precursors which are usually assigned to the groups A, B, C, E, F and H are preferred for the purposes of the invention.

The substances known as vitamin A include retinol (vitamin $A_1$) and 3,4-didehydroretinol (vitamin $A_2$). β-Carotene is the provitamin of retinol. According to the invention, the vitamin A component may be selected, for example, from vitamin A acid and esters thereof, vitamin A aldehyde and vitamin A alcohol and esters thereof, such as the palmitate and the acetate. The preparations used in accordance with the invention preferably contain the vitamin A component in quantities of 0.05 to 1% by weight, based on the preparation applied as a whole.

The vitamin B group or the vitamin B complex includes inter alia
vitamin $B_1$ (thiamin)
vitamin $B_2$ (riboflavin)
vitamin $B_3$. The compounds nicotinic acid and nicotinic acid amide (niacin amide) are often referred to by this name. Nicotinic acid amide is preferred for the purposes of the invention and is present in the preparations used in accordance with the invention in quantities of preferably 0.05 to 1% by weight, based on the preparation as a whole.
vitamin $B_5$ (pantothenic acid, pantenol and pantolactone). Within this group, panthenol and/or pantolactone is/are preferably used. Panthenol derivatives suitable for use in accordance with the invention are, in particular, the esters and ethers of panthenol and cationically derivatized panthenols. Individual representatives are, for example, panthenol triacetate, panthenol monoethyl ether and its monoacetate and the cationic phenol derivatives disclosed in WO 92/13829. The above-mentioned compounds of the vitamin $B_5$ type are present in the compositions according to the invention in quantities of preferably 0.05 to 10% by weight and, more particularly, 0.1 to 5% by weight, based on the preparation applied as a whole.
vitamin $B_6$ (pyridoxine and pyridoxamine and pyridoxal). The vitamin $B_6$ compounds mentioned are preferably present in the compositions according to the invention in quantities of 0.01 to 5% by weight, based on the preparation applied as a whole. Quantities of 0.05 to 1% by weight are particularly preferred.

Vitamin C (ascorbic acid). Vitamin C is present in the compositions used in accordance with the invention in quantities of preferably 0.1 to 3% by weight, based on the preparation applied as a whole. Its use in the form of the palmitic acid esters, the glucosides or phosphates can be preferred. Its use in combination with tocopherols can also be preferred.

Vitamin E (tocopherols, more particularly α-tocopherol). Tocopherol and its derivatives, including, in particular, the esters, such as the acetate, the nicotinate, the phosphate and the succinate, are present in the compositions according to the invention in quantities of preferably 0.05 to 1% by weight, based on the preparation applied as a whole.

Vitamin F. The term "Vitamin F" is normally applied to essential fatty acids, more particularly linoleic acid, linolenic acid and arachidonic acid.

Vitamin H. Vitamin H is the compound (3aS,4S,6aR)-2-oxohexahydrothienol[3,4-d]-imidazole-4-valeric acid which is now known by the trivial name of biotin. Biotin is present in the compositions according to the invention in quantities of preferably 0.0001 to 1.0% by weight and, more particularly, 0.001 to 0.01% by weight, based on the preparation applied as a whole.

The two-component compositions according to the invention preferably contain vitamins, provitamins and vitamin precursors from the groups A, B, E and H.

Panthenol, pantolactone, pyridoxine and derivatives thereof and nicotinic acid amide and biotin are particularly preferred.

In a fifth preferred embodiment, the two-component compositions according to the invention contain at least one plant extract.

These extracts are normally prepared by extraction of the whole plant. In individual cases, however, it can also be preferred to prepare the extracts solely from flowers and/or leaves of the plant.

So far as the plant extracts preferably used in accordance with the invention are concerned, reference is made in particular to the extracts listed in the Table beginning on page 4 of the 3rd edition of the Leiffaden zur Inhaltstoffdeklaration kosmetischer Mittel, published by the Industrieverband Körperpflege-und Waschmittel e.V. (IKW), Frankfurt.

Extracts preferred for the purposes of the invention are, above all, extracts of green tea, oak bark, stinging nettle, hamamelis, hops, henna, camomile, burdock root, horse willow, hawthorn, lime blossom, almond, aloe vera, pine needle, horse chestnut, sandalwood, juniper, coconut, mango, apricot, lemon, wheat, kiwi, melon, orange, grapefruit, sage, rosemary, birch, mallow, lady's smock, creeping thyme, yarrow, thyme, balm, restharrow, coltsfoot, hibiscus, meristem, ginseng and ginger root.

Particularly preferred extracts are extracts of green tea, oak bark, stinging nettle, hamamelis, hops, camomile, burdock root, horse willow, lime blossom, almond, aloe vera, coconut, mango, apricot, lemon, wheat, kiwi, melon, orange, grapefruit, sage, rosemary, birch, lady's smock, creeping thyme, yarrow, restharrow, meristem, ginseng and ginger root.

Extracts of green tea, almond, aloe vera, coconut, mango, apricot, lemon, wheat, kiwi and melon are most particularly suitable.

Suitable extractants for preparing the plant extracts mentioned above are water, alcohols and mixtures thereof. Preferred alcohols are lower alcohols, such as ethanol and isopropanol, but especially polyhydric alcohols, such as ethylene glycol and propylene glycol, either as sole extractant or in combination with water. Plant extracts based on water/propylene glycol in a ratio of 1:10 to 10:1 have proven to be particularly suitable.

According to the invention, the plant extracts may be used both in pure form and in dilute form. If they are used in dilute form, they normally contain ca. 2 to 80% by weight active substance and—as solvent—the extractant or extractant mixture used in their preparation.

In another preferred embodiment, mixtures of several, more particularly two, different plant extracts may be used in the preparations according to the invention.

In a sixth embodiment, the two-component compositions according to the invention contain at least one carboxylic acid as the care component.

Short-chain carboxylic acids, in particular, may be used advantageously in accordance with the invention. In the context of the invention, short-chain carboxylic acids and derivatives thereof are understood to be carboxylic acids which may be saturated or unsaturated and/or linear or branched or cyclic and/or aromatic and/or heterocyclic and which have a molecular weight below 750. Saturated or unsaturated, linear or branched carboxylic acids with a chain length of 1 to 16 carbon atoms are preferred for the purposes of the invention, those with a chain length of 1 to 12 carbon atoms being most particularly preferred.

According to the invention, the short-chain carboxylic acids may contain one, two, three or more carboxy groups. Carboxylic acids containing several carboxy groups, more particularly, di- and tricarboxylic acids, are preferred for the purposes of the invention. The carboxy groups may be completely or partly present as ester, anhydride, lactone, amide, imido acid, lactam, lactime, dicarboximide, carbohydrazide, hydrazone, hydroxam, hydroxime, amidine, amidoxime, nitrile, phosphonic or phosphate ester. The carboxylic acids usable in accordance with the invention may of course be substituted along the carbon chain or the ring. The substituents of the carboxylic acids usable in accordance with the invention include, for example, $C_1$ alkyl, $C_{2-8}$ alkenyl, aryl, aralkyl and aralkenyl, hydroxymethyl, $C_{2-8}$ hydroxyalkyl, $C_{2-8}$ hydroxyalkenyl, aminomethyl, $C_{2-8}$ aminoalkyl, cyano, formyl, oxo, thioxo, hydroxy, mercapto, amino, carboxy or imino groups. Preferred substituents are $C_{1-8}$alkyl, hydroxymethyl, hydroxy, amino and carboxy groups. Substituents in the α-position are particularly preferred. Most particularly preferred substituents are hydroxy, alkoxy and amino groups, the amino function optionally being further substituted by alkyl, aryl, aralkyl and/or alkenyl groups. Other preferred carboxylic acid derivatives are the phosphonic and phosphate esters.

Examples of carboxylic acids usable in accordance with the invention are formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphor acid, benzoic acid, o,m,p-phthalic acid, naphthoic acid, toluylic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrole carboxylic acid, 1,2,4,6,7-naphthalene pentaacetic acid, malonaldehydic acid, 4-hydroxyphthalamido acid, 1-pyrazole carboxylic acid, gallic acid or propane tricarboxylic acid, a dicarboxylic acid selected from the group consisting of compounds corresponding to general formula (N-I):

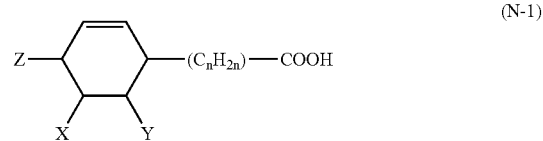

(N-I)

in which Z represents a linear or branched alkyl or alkenyl group containing 4 to 12 carbon atoms, n is a number of 4 to 12 and one of the two groups X and Y represents a COOH group and the other represents hydrogen or a methyl or ethyl group, dicarboxylic acids corresponding to general formula (N-I) which additionally contain 1 to 3 methyl or ethyl substituents on the cyclohexene ring and dicarboxylic acids which formally are formed from the dicarboxylic acids (N-I) by addition of one molecule of water onto the double bond in the cyclohexene ring.

Dicarboxylic acids corresponding to formula (N-I) are known in the literature. One process for their production is disclosed, for example, in U.S. Pat. No. 3,753,968.

The dicarboxylic acids corresponding to formula (N-I) may be obtained, for example, by reaction of polyunsaturated dicarboxylic acids with unsaturated monocarboxylic acids in the form of a Diels-Alder cyclization. A polyunsaturated fatty acid is normally used as the starting dicarboxylic acid component. Linoleic acid obtainable from natural fats and oils is preferred. Preferred monocarboxylic acid components are, in particular, acrylic acid and, for example, methacrylic acid and crotonic acid. Isomer mixtures where one component is present in excess are normally formed in Diels-Alder reactions. According to the invention, these isomer mixtures may be used in the same way as the pure compounds.

Besides the preferred dicarboxylic acids of formula (N-I), dicarboxylic acids which differ from the compounds of formula (N-I) in the presence of 1 to 3 methyl or ethyl substituents on the cyclohexyl ring or which, formally, are formed from these compounds by addition of one molecule of water onto the double bond of the cyclohexene ring may also be used in accordance with the invention.

The dicarboxylic acid mixture obtainable by reaction of linoleic acid with acrylic acid has proven to be particularly effective for the purposes of the invention. It is a mixture of 5- and 6-carboxy-4-hexyl-2-cyclohexene-1-octanoic acid. Such compounds are commercially obtainable under the names of Westvaco Diacid® 1550 and Westvaco Diacid® 1595 (manufacturer: Westvaco).

Besides the short-chain carboxylic acids according to the invention themselves, as mentioned by way of example in the foregoing, physiologically compatible salts thereof may also be used in accordance with the invention. Examples of such salts are the alkali metal and alkaline earth metal salts, zinc salts and ammonium salts, which—in the context of the present invention—also include the mono-, di- and trimethyl, -ethyl and -hydroxyethyl ammonium salts. However, acids neutralized with alkaline reacting amino acids, for example, arginine, lysine, ornithine and histidine, are most particularly preferred for the purposes of the invention. In addition, it may be preferable for formulation reasons to select the carboxylic acid from the water-soluble representatives, more particularly the water-soluble salts.

In another preferred embodiment of the invention, 2-pyrrolidinone-5-carboxylic acid and derivatives thereof may be used as the carboxylic acid. The sodium, potassium, calcium, magnesium or ammonium salts, in which the ammonium ion carries one to three $C_{1-4}$ alkyl groups besides hydrogen, are particularly preferred. The sodium salt is most particularly preferred. The quantities used in the compositions according to the invention are preferably, 0.05 to 10% by weight, more preferably, 0.1 to 5% by weight and most preferably, 0.1 to 3% by weight, based on the preparation applied as a whole.

Another preferred embodiment of the invention is characterized by the use of hydroxycarboxylic acids, more especially dihydroxy-, trihydroxy- and polyhydroxycarboxylic acids and dihydroxy-, trihydroxy- and polyhydroxydi-, tri- and polycarboxylic acids. It has been found in this regard that, besides, the hydroxycarboxylic acids, the hydroxycarboxylic acid esters and the mixtures of hydroxycarboxylic acids and esters thereof and polymeric hydroxycarboxylic acids and esters thereof can also be particularly advantageous. Preferred hydroxycarboxylic acid esters are, for example, full esters of glycolic acid, lactic acid, malic acid, tartaric acid or citric acid. Other basically suitable hydroxycarboxylic acid esters are esters of β-hydroxypropionic acid, tartronic acid, D-gluconic acid, saccharic acid, mucic acid or glucuronic acid. Suitable alcohol components of these esters are primary, linear or branched aliphatic alcohols containing 8 to 22 carbon atoms, i.e., for example, fatty alcohols or synthetic fatty alcohols. The esters of $C_{12-15}$ fatty alcohols are particularly preferred. Esters of this type are commercially obtainable, for example, under the name of Cosmacol® from EniChem, Augusta Indiustriale. Particularly preferred polyhydroxypolycarboxylic acids are polylactic acid and polytartaric acid and esters thereof.

In a seventh preferred embodiment, the two-component compositions according to the invention contain at least one protein hydrolyzate and/or a derivative thereof as the care component.

Protein hydrolyzates are product mixtures obtained by acid-, base- or enzyme-catalyzed degradation of proteins. In the context of the invention, protein hydrolyzates are also understood to be total hydrolyzates and individual amino acids and derivatives thereof and mixtures of different amino acids. In addition, polymers made up of amino acids and amino acid derivatives are also protein hydrolyzates in the context of the present invention and include, for example, polyalanine, polyasparagine, polyserine, etc. Other examples of compounds suitable for use in accordance with the invention are L-alanyl-L-proline, polyglycine, glycyl-L-glutamine or D/L-methionine-5-methyl sulfonium chloride. β-Amino acids and derivatives thereof, such as β-alanine, anthranilic acid or hippuric acid, may of course also be used in accordance with the invention. The molecular weight of the protein hydrolyzates usable in accordance with the invention is between 75, the molecular weight of glycine, and 200,000, preferably between 75 and 50,000 and more particularly between 75 and 20,000 dalton.

According to the invention, protein hydrolyzates of both vegetable and animal or marine or synthetic origin may be used.

Animal protein hydrolyzates are, for example, elastin, collagen, keratin, silk and milk protein hydrolyzates which may also be present in the form of salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co.), Lexein® (Inolex), Sericin (Pentapharm) and Kerasol® (Croda).

The use of silk protein hydrolyzates is particularly interesting. Silk is understood to be the fibers of the cocoon of the silkworm moth (*Bombyx mori* L.). The raw silk fiber consists of a double strand of fibroin. As a cement substance, sericin holds this double strand together. 70 to 80% by weight of silk consists of fibroin, 19 to 28% by weight of sericin, 0.5 to 1% by weight of fat and 0.5 to 1% by weight of dyes and mineral constituents.

The principal constituents of sericin at ca. 46% by weight are hydroxyamino acids. Sericin consists of a group of 5 to 6 proteins. The principal amino acids of sericin are serine (Ser, 37% by weight), aspartate (Asp, 26% by weight), glycine (Gly, 17% by weight), alanine (Ala), leucine (Leu) and tyrosine (Tyr).

Fibroin, which is insoluble in water, is one of the scleroproteins with a long-chain molecular structure. The principal constituents of fibroin are glycine (44% by weight), alanine (26% by weight) and tyrosine (13% by weight). Another key structural feature of fibroin is the hexapeptide sequence Ser-Gly-Ala-Gly-Ala-Gly.

Technically, it is readily possible to separate the two silk proteins from one another. It is therefore not surprising that both sericin and fibroin are known individually for use in cosmetic products. In addition, protein hydrolyzates and derivatives based on the individual silk proteins are known raw materials in cosmetic preparations. For example, sericin as such is marketed as Sericin Code 303-02 by Pentapharm Ltd. However, fibroin is marketed far more frequently as a protein hydrolyzate with different molecular weights. These hydrolyzates are marketed, in particular, as "silk hydrolyzates." Thus, hydrolyzed fibroin with average molecular weights of 350 to 1,000 is marketed, for example, under the name of Promois® Silk. DE-A-31 39 438 A1 also describes colloidal fibroin solutions as an additive for cosmetic preparations.

The positive properties of the silk protein derivatives from sericin and fibroin are known individually from the literature. Thus, the sales brochure of Pentapharm Ltd. describes the cosmetic effects of sericin on the skin as soothing, hydrating and film-forming. DE-A-31 39 438 A1, for example, describes a fibroin derivative as having a hair-care and hair-conditioning effect. In addition, according to DE 102 40 757 A1, the simultaneous use of sericin and fibroin or derivatives and/or hydrolyzates thereof leads to a synergistic increase in the positive effects of the silk proteins and their derivatives.

Accordingly, an active-component complex (A) consisting of the active component (A1) selected from sericin, sericin hydrolyzates and/or derivatives and mixtures thereof and an active component (A2) selected from fibroin and/or fibroin hydrolyzates and/or derivatives and/or mixtures thereof is used as the silk protein hydrolyzate in the two-component composition according to the invention.

The active-component complex (A) used in accordance with the invention synergistically improves the above-mentioned key inner and outer structural features and the strength and elasticity of human hair to a significant extent.

The following may be used as active components (A1) in the active-component complex (A):

- sericin,
- hydrolyzed and/or further derivatized sericin, such as, for example, commercial products with the INCI names Sericin, Hydrolyzed Sericin or Hydrolyzed Silk,
- a mixture of the amino acids serine, aspartate and glycine and/or methyl, propyl, iso-propyl, butyl, isobutyl esters thereof, salts thereof, such as, for example, hydrochlorides, sulfates, acetates, citrates, tartrates, this mixture containing 20 to 60% by weight of serine and/or serine derivatives, 10 to 40% by weight of aspartate and/or aspartate derivatives and 5 to 30% by weight of glycine and/or glycine derivatives, provided that the quantities of these amino acids and/or their derivatives add up to 100% by weight,
- and mixtures thereof.

The following may be used as active components (A2) in the active-component complex (A):

- native fibroin converted into a soluble form,
- hydrolyzed and/or further derivatized fibroin, more particularly partly hydrolyzed fibroin, which contains the amino acid sequence Ser-Gly-Ala-Gly-Ala-Gly as its principal constituent,
- the amino acid sequence Ser-Gly-Ala-Gly-Ala-Gly,
- a mixture of the amino acids glycine, alanine and tyrosine and/or methyl, propyl, iso-propyl, butyl, iso-butyl esters thereof, salts thereof, such as, for example, hydrochlorides, sulfates, acetates, citrates, tartrates, this mixture containing 20 to 60% by weight of glycine and/or glycine derivatives, 10 to 40% by weight of alanine and/or alanine derivatives and 0 to 25% by weight of tyrosine and/or tyrosine derivatives, provided that the quantities of these amino acids and/or their derivatives add up to 100% by weight,
- and mixtures thereof.

Particularly good care properties can be obtained by using one of the two active components of the active-component complex (A) in its native or solubilized form. A mixture of several active components (A1) and/or (A2) may also be used.

In a preferred embodiment, the two active components (A1) and (A2) may be used in a ratio of 10:90 to 70:30, more particularly 15:85 to 50:50 and most particularly 20:80 to 40:60, based on the respective contents of active component in the two-component compositions according to the invention.

The derivatives of the sericin and fibroin hydrolyzates include both anionic and cationized protein hydrolyzates. The protein hydrolyzates of sericin and fibroin and the derivatives prepared from them may be obtained from the corresponding proteins by chemical, more particularly alkaline or acidic, hydrolysis, by enzymatic hydrolysis and/or by a combination of both types of hydrolysis. The hydrolysis of proteins generally gives a protein hydrolyzate with a molecular weight distribution of ca. 100 dalton to several thousand dalton. Preferred protein hydrolyzates of sericin and fibroin and/or derivatives thereof are those of which the basic protein has a molecular weight of 100 to 25,000 dalton, preferably 250 to 10,000 dalton. Cationic protein hydrolyzates of sericin and fibroin also include quaternized amino acids and mixtures thereof. The quaternization of the protein hydrolyzates or the amino acids is often carried out with quaternary ammonium salts, such as, for example, N,N-dimethyl-N-(n-alkyl)-N-(2-hydroxy-3-chloro-n-propyl)-ammonium halides. In addition, the cationic protein hydrolyzates may even be further derivatized. Typical examples of the cationic protein hydrolyzates and derivatives usable in accordance with the invention are the commercially available products mentioned under their INCI names in "International Cosmetic Ingredient Dictionary and Handbook" (7th Edition, 1997, The Cosmetic, Toiletry and Fragrance Association, 1101 17th Street, N.W., Suite 300, Washington, D.C. 20036-4702): Cocodimonium Hydroxypropyl Hydrolyzed Silk, Cocodimonium Hydroxypropyl Silk Amino Acids, Hydroxyproypitrimonium Hydrolyzed Silk, Lauryldimonium Hydroxypropyl Hydrolyzed Silk, Steardimonium-Hydroxypropyl-Hydrolyzed Silk, Quaternium-79 Hydrolyzed Silk. Typical examples of the anionic protein hydrolyzates and derivatives thereof according to the invention are the commercially available products mentioned under their INCI names in "International Cosmetic Ingredient Dictionary and Handbook" (7th Edition, 1997, The Cosmetic, Toiletry and Fragrance Association, 1101 17th Street, N.W., Suite 300, Washington, D.C. 20036-4702): Potassium Cocoyl Hydrolyzed Silk, Sodium Lauroyl Hydrolyzed Silk or Sodium Stearoyl Hydrolyzed Silk. Finally, typical examples of the sericin and fibroin derivatives usable in accordance with the invention are the products commercially obtainable under their INCI names: Ethyl Ester of Hydrolyzed Silk and Hydrolyzed Silk PG-Propyl Methylsilanediol. Also suitable for use in accordance with the invention, but not necessarily preferred, are the commercially available products with the INCI names Palmitoyl Oligopeptide, Palmitoyl Pentapeptide-3, Palmitoyl Pentapeptide-2, Acetyl Hexapeptide-1, Acetyl Hexapeptide-3, Copper Tripeptide-1, Hexapeptide-1, Hexapeptide-2, MEA-Hydrolyzed Silk.

The effect of the active-component complex (A) according to the invention can be further enhanced by the addition of fatty compounds. Fatty compounds are understood to be fatty acids, fatty alcohols, natural and synthetic waxes, which may be present both in solid form and in liquid form as aqueous dispersions, and natural and synthetic cosmetic oil components.

According to the invention, it is preferred to use protein hydrolyzates of vegetable origin, for example, soya, almond, pea, potato and wheat protein hydrolyzates. Such products are obtainable, for example, under the names of Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Although the use of the protein hydrolyzates as such is preferred, amino acid mixtures obtained otherwise may optionally be used in their place. Derivatives of the protein hydrolyzates, for example, in the form of their fatty acid condensation products, may also be used. Such products are marketed, for example, under the names of Lamepon® (Cognis), Lexein® (Inolex), Crolastin® (Croda), Crosilk® (Croda) or Crotein® (Croda).

The teaching according to the invention does, of course, encompass all isomeric forms, such as cis-trans isomers, diastereomers and chiral isomers.

According to the invention, a mixture of several protein hydrolyzates may also be used.

The protein hydrolyzates are present in the two-component compositions according to the invention in concentrations of, for example, 0.01% by weight to 20% by weight, preferably in concentrations of 0.05% by weight to 15% by weight and more particularly in concentrations of 0.05% by weight to 5% by weight, based on the preparation applied as a whole.

In an eighth preferred embodiment, the preparations according to the invention contain ectoin or ectoin derivatives, allantoin, taurine and/or bisabolol as the care component.

In the context of the invention, "ectoin and ectoin derivatives" are understood to be compounds corresponding to formula (IV):

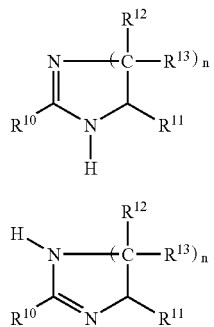

(IVa)

(IVb)

in which $R^{10}$ is a hydrogen atom, a branched or unbranched $C_{1-4}$ alkyl group or a $C_{2-4}$ hydroxyalkyl group, $R^{11}$ is a hydrogen atom, a —$COOR^{14}$ group or a —CO(NH) $R^{14}$ group, where $R^{14}$ is a hydrogen atom, a $C_{1-4}$ alkyl group, an amino acid residue, a dipeptide or a tripeptide residue, $R^{12}$ and $R^{13}$ independently of one another represent a hydrogen atom, a $C_{1-4}$ alkyl group or a hydroxy group, with the proviso that the two substituents cannot both be a hydroxy group, and n is an integer of 1 to 3, and/or physiologically compatible salts thereof and/or an isomeric or stereoisomeric form.

Suitable physiologically compatible salts of the general compounds of formula (IVa) or (IVb) are, for example, the alkali metal, alkaline earth metal, ammonium, triethylamine or tris-(2-hydroxyethyl)-amine-salts and those arising out of the reaction of compounds corresponding to formula (IVa) or (IVb) with inorganic and organic acids, such as hydrochloric acid, phosphoric acid, sulfuric acid, branched or unbranched, substituted or unsubstituted (for example, by one or more hydroxy groups), $C_{1-4}$ mono- or dicarboxylic acids, aromatic carboxylic acids and sulfonic acids, such as acetic acid, citric acid, benzoic acid, maleic acid, fumaric acid, tartaric acid and p-toluenesulfonic acid. Examples of particularly preferred physiologically compatible salts are the Na, K, Mg and Ca and ammonium salts of compounds (IVa) or (IVb) and the salts formed by reaction of compounds corresponding to formula (IVa) or (IVb) with hydrochloric acid, acetic acid, citric acid and benzoic acid.

In the context of the invention isomeric or stereoisomeric forms of the compounds of formula (IVa) or (IVb) are understood to be any optical isomers, diastereomers, racemates, zwitterions, cations or mixtures thereof.

Amino acids are understood to be the stereoisomeric forms, for example, D- and L-forms, of the following compounds: asparagine, arginine, aspartic acid, glutamine, glutamic acid, β-alanine, γ-aminobutyrate, $N_\epsilon$-acetyl lysine, $N_\delta$-acetyl ornithine, $N_\gamma$-acetyl diaminobutyrate, $N_\alpha$-acetyl diaminobutyrate, histidine, isoleucine, leucine, methionine, phenyl alanine, serine, threonine and tyrosine.

L-amino acids are preferred. Amino acid residues are derived from the corresponding amino acids. The following amino acid residues are preferred: Gly, Ala, Ser, Thr, Val, β-ala, γ-aminobutyrate, Asp, Glu, Asn, Aln, $N_\epsilon$-acetyl lysine, $N_\delta$-acetyl ornithine, $N_\gamma$-acetyl diaminobutyrate, $N_\alpha$-acetyl diaminobutyrate.

The abbreviated notation of the amino acids follows the standard notation. The di- or tripeptide residues are by their chemical nature acid amides and decompose on hydrolysis into 2 or 3 amino acids. The amino acids in the di- or tripeptide residue are attached to one another by amide bonds.

So far as the production of the di- and tripeptide residues is concerned, reference is expressly made to EP 0 671 161 A1 (Marbert). Examples of di- and tripeptide residues can also be found in the disclosure of EP 0 671 161 A1.

Examples of $C_{1-4}$ alkyl groups in the compounds according to the invention are methyl, ethyl, n-propyl, isopropyl, n-butyl, isobutyl and tertbutyl. Preferred alkyl groups are methyl and ethyl. Methyl is a particularly preferred alkyl group. Preferred $C_{2-4}$ hydroxyalkyl groups are the 2-hydroxyethyl, 3-hydroxypropyl or 4-hydroxybutyl groups; 2-hydroxyethyl is a particularly preferred hydroxyalkyl group.

The two-component compositions according to the invention contain these care components in quantities of preferably 0.001 to 2% by weight, and more particularly, 0.01 to 0.5% by weight, based on the preparation applied as a whole.

In a ninth preferred embodiment, preparation (B) contains at least one mono- or oligosaccharide as the care component.

Both monosaccharides and oligosaccharides, such as cane sugar, lactose and raffinose, for example, may be used. Monosaccharides are preferred for the purposes of the invention. Of the monosaccharides, compounds containing 5 or 6 carbon atoms are preferred.

Suitable pentoses and hexoses are, for example, ribose, arabinose, xylose, lyxose, allose, altrose, glucose, mannose, gulose, idose, galactose, talose, fucose and fructose. Arabinose, glucose, galactose and fructose are preferred carbohydrates. Glucose both in the D-(+) and the L-(−) configuration is most particularly preferred.

Derivatives of these pentoses and hexoses, such as the corresponding onic and uronic acids (sugar acids), sugar alcohols and glycosides may also be used for the purposes of the invention. Preferred sugar acids, are gluconic acid, glucuronic acid, saccharic acid, mannosaccharic acid and mucic acid. Preferred sugar alcohols are sorbitol, mannitol and dulcitol. Preferred glycosides are the methyl glucosides.

Since the mono- and oligosaccharides used are normally obtained from natural raw materials, such as starch, they generally have the configurations corresponding to those raw materials (for example, D-glucose, D-fructose and D-galactose).

The mono- and oligosaccharides are present in the hair treatment compositions according to the invention in a quantity of preferably 0.1 to 8% by weight, and more particularly, in a quantity of 1 to 5% by weight, based on the preparation applied as a whole.

In a tenth embodiment, the two-component composition according to the invention contains at least one silicone oil and/or at least one silicone gum as the care component.

Silicones or silicone gums suitable for the purposes of the invention are, in particular, dialkyl and alkylaryl siloxanes such as, for example, dimethyl polysiloxane and methylphenyl polysiloxane and alkoxylated, quaternized and anionic derivatives thereof.

Examples of such silicones are
- oligomeric polydimethyl cyclosiloxanes (INCI name: Cyclomethicone), more particularly the tetrameric and the pentameric compounds which are marketed by Dow Corning under the names of DC 344 and DC 345,
- hexamethyl disiloxane (INCI name: Hexamethyldisiloxane), for example, the product marketed under the name of Abil® K 520,
- polymeric polydimethyl siloxanes (INCI name: Dimethicone), for example, the products marketed by Dow Corning under the name of DC 200,
- polyphenyl methyl siloxanes (INCI name: Phenyl Trimethicone), for example, the product marketed by Dow Corning under the name of DC 556 Fluid,
- silicone/glycol copolymers (INCI name: Dimethicone Copolyol), for example, the Dow Corning products DC 190 and DC 193,
- esters and partial esters of silicone/glycol copolymers as marketed, for example, by Fanning under the name of Fancorsil® LIM (INCI name: Dimethicone Copolyol Meadowfoamate),
- hydroxy-terminated dimethyl siloxanes (INCI name: Dimethiconol), for example, the Dow Corning products DC 1401 and Q2-1403,
- aminofunctional polydimethylsiloxanes and hydroxyamino-modified silicones (INCI name: inter alia, Amodimethicone and Quaternium-80), such as the commercial products XF42-B1989 (manufacturer: GE Toshiba Silicones), Q2-7224 (manufacturer: Dow Corning; a stabilized trimethyl silyl amodimethicone), Dow Corning® 939 Emulsion (containing a hydroxylamino-modified silicone also known as Amodimethicone), SM-2059 (manufacturer: General Electric), SLM-55067 (manufacturer: Wacker) and Abil®-Quat 3270 and 3272 (manufacturer: Th. Goldschmidt),
- anionic silicone oils, such as the product Dow Corning® 1784 for example,
- aminomodified organosilicones, such as the product Abil Soft A843 (manufacturer: Osi Specialities), for example.

In a preferred embodiment, the preparations according to the invention contain a combination of a volatile and a nonvolatile silicone. Volatile silicones in the context of the invention are silicones which have a volatility equal to or higher than that of the cyclic, pentameric dimethyl siloxane. Such combinations are also obtainable as commercial products (for example, Dow Corning® 1401, Dow Corning® 1403 and Dow Corning® 1501—mixtures of a cyclomethicone and a dimethiconol).

In a particularly preferred embodiment, preparation (B) contains a dialkyl polysiloxane or a derivative thereof as the care component. Preferred alkyl groups are methyl, ethyl, i-propyl and n-propyl. Dimethyl polysiloxane or a derivative thereof is particularly preferred. Aminofunctional derivatives of dimethyl polysiloxane are preferred. A most particularly preferred derivative is commercially available under the INCI name of Amodimethicone.

The preparations according to the invention preferably contain the silicones in quantities of 0.01 to 10% by weight and more particularly in quantities of 0.1 to 5% by weight, based on the preparation applied as a whole.

In an eleventh embodiment, preparation (B) contains at least one lipid as the care component.

Lipids suitable for the purposes of the invention are phospholipids, for example, soya lecithin, egg lecithin and kephalins and the substances known under the INCI names of Linoleamidopropyl PG-Dimonium Chloride Phosphate, Cocamidopropyl PG-Dimonium Chloride Phosphate and Stearamidopropyl PG-Dimonium Chloride Phosphate. These substances are marketed, for example, by the Mona Company under the names of Phospholipid EFA®, Phospholipid PTC® and Phospholipid SV®.

The preparations according to the invention preferably contain the lipids in quantities of 0.01 to 10% by weight and more particularly in quantities of 0.1 to 5% by weight, based on the preparation applied as a whole.

In a twelfth embodiment, preparation (B) contains at least one oil component as the care component.

Natural and synthetic cosmetic oil components include, for example,
- vegetable oils. Examples of such oils include sunflower oil, olive oil, soybean oil, rapeseed oil, almond oil, jojoba oil, orange oil, wheatgerm oil, peach kernel oil and the liquid fractions of coconut oil. However, other triglyceride oils, such as the liquid fractions of bovine tallow, and synthetic triglyceride oils are also suitable.
- liquid paraffin oils, isoparaffin oils and synthetic hydrocarbons and di-n-alkyl ethers containing a total of 12 to 36 carbon atoms and, more particularly, 12 to 24 carbon atoms, such as, for example, di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether and ditert.butyl ether, diisopentyl ether, di-3-ethyldecyl ether, tertbutyl-n-octyl ether, isopentyl-n-octyl ether and 2-methylpentyl-n-octyl ether. The compounds 1,3-di-(2-ethylhexyl)-cyclohexane and di-n-octyl ether obtainable as commercial products (Cetiol® S and Cetiol® OE, respectively) can be preferred.
- ester oils. Esters oils are understood to be the esters of $C_{6-30}$ fatty acids with $C_{2-30}$ fatty alcohols. The monoesters of fatty acids with alcohols containing 2 to 24 carbon atoms are preferred. Examples of the fatty acid components used in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the oxidation of aldehydes from Roelen's oxosynthesis or in the dimerization of unsaturated fatty acids. Examples of the fatty alcohol components in the ester oils are isopropyl alcohol, caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols. According to the invention, isopropyl myristate (Rilanit® IPM), isononanoic acid $C_{16-18}$ alkyl ester (Cetiol® SN), 2-ethylhexyl palmitate (Cegesoft® 24), stearic acid-2-ethylhexyl ester (Cetiol® 868), cetyl oleate, glycerol tricaprylate, cocofatty alcohol caprate/caprylate (Cetiol® LC), n-butyl stearate, oleyl erucate (Cetiol® J 600), isopropyl palmitate (Rilanit® IPP), Oleyl Oleate (Cetiol®), lauric acid hexyl ester (Cetiol® A), di-n-butyl adipate (Cetiol® B), myristyl myristate (Cetiol® MM), Cetearyl Isononanoate (Cetiol® SN), oleic acid decyl ester (Cetiol® V) are particularly preferred.

dicarboxylic acid esters, such as di-n-butyl adipate, di-(2-ethylhexyl)-adipate, di-(2-ethylhexyl)-succinate and diisotridecyl acelate, and diol esters, such as ethylene glycol dioleate, ethylene glycol diisotridecanoate, propylene glycol di-(2-ethylhexanoate), propylene glycol diisostearate, propylene glycol dipelargonate, butanediol diisostearate, neopentyl glycol dicaprylate, symmetrical, nonsymmetrical or cyclic esters of carbonic acid with fatty alcohols as described, for example, in DE-OS 197 56 454, glycerol carbonate or dicaprylyl carbonate (Cetiol® CC), trifatty acid esters of saturated and/or unsaturated linear and/or branched fatty acids with glycerol, fatty acid partial glycerides, i.e. monoglycerides, diglycerides and technical mixtures thereof. Where technical products are used, small quantities of triglycerides may also be present from the production process. The partial glycerides preferably correspond to formula (D4-I):

(D4-1))

in which $R^1$, $R^2$ and $R^3$ independently of one another represent hydrogen or a linear or branched, saturated and/or unsaturated acyl group containing 6 to 22 and preferably 12 to 18 carbon atoms, with the proviso that at least one of these substituents is an acyl group and at least one is hydrogen. The sum (m+n+q) is 0 or a number of 1 to 100 and preferably 0 or a number of 5 to 25. Preferably, $R^1$ is an acyl group and $R^2$ and $R^3$ are hydrogen atoms and the sum (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Oleic acid monoglycerides are preferably used.

The quantity in which the natural and synthetic cosmetic oil components are used in the two-component compositions according to the invention is typically 0.1 to 30% by weight, based on the preparation applied as a whole, preferably 0.1 to 20% by weight and more particularly 0.1 to 15% by weight.

In a thirteenth embodiment, preparation (B) contains an enzyme as the care component. Particularly preferred enzymes for the purposes of the invention are selected from a group consisting of proteases, lipases, transglutaminase, oxidases and peroxidases.

In a fourteenth embodiment, the two-component compositions according to the invention contain at least one pearl extract.

Pearls from mussels consist essentially of inorganic and organic calcium salts, trace elements and proteins. Pearls can be obtained readily from cultivated mussels. The mussels may be cultivated both in fresh water and in sea water. This can affect the ingredients of the pearls. A pearl extract emanating from mussels cultivated in sea water or fresh water is preferred for the purposes of the invention. The pearls consist to a large extent of aragonite (calcium carbonate), conchiolin and an albuminoid. The latter constituents are proteins. Pearls also contain magnesium and sodium salts, inorganic silicon compounds and phosphates.

To produce the pearl extract, the pearls are pulverized. The pulverized pearls are then extracted by the usual methods. Water, alcohols and mixtures thereof may be used as extractants for producing the pearl extracts. The water may be both demineralized water and sea water. Preferred alcohols are lower alcohols, such as ethanol and isopropanol, but especially polyhydric alcohols, such as glycerol, diglycerol, triglycerol, polyglycerol, ethylene glycol, propylene glycol and butylene glycol, both as sole extractant and in admixture with demineralized water or sea water. Pearl extracts based on water/glycerol mixtures have proven to be particularly suitable. Depending on the extraction conditions, the pearl proteins (conchiolin and albuminoid) may be present very largely in the native state or even partly or very largely as protein hydrolyzates. A pearl extract in which conchiolin and albuminoid are already partly hydrolyzed is preferred. The essential amino acids of these proteins are glutamic acid, serine, alanine, glycine, aspartic acid and phenylalanine. In another particularly preferred embodiment, the pearl extract is advantageously additionally enriched with at least one or more of these amino acids. In the most preferred embodiment, the pearl extract is enriched with glutamic acid, serine and leucine. In addition, the extract contains a more or less large percentage of minerals and trace elements, depending on the extraction conditions and, more particularly, on the choice of extractant. A preferred extract contains organic and/or inorganic calcium salts and also magnesium and sodium salts, inorganic silicon compounds and/or phosphates. A most particularly preferred pearl extract contains at least 75%, preferably 85%, more preferably 90% and most preferably 95% of all the ingredients of naturally occurring pearls. Examples of pearl extracts usable in accordance with the invention are the commercial products Pearl Protein Extract BG® or Crodarom® Pearl.

The pearl extracts described above are preferably present in a quantity of at least 0.01 to 20% by weight. Quantities of the extract of 0.01 to 10% by weight are preferred, quantities of 0.01 to 5% by weight, based on the two-component composition as a whole, being most particularly preferred.

Although each of the care components mentioned in the various embodiments gives a satisfactory result on its own, the present invention also encompasses embodiments where preparation (B) also contains several care components from the various groups.

The two-component composition according to the invention is made up in various compartments of a multicompartment tube. The multicompartment tube is preferably a two-compartment tube, a first compartment holding preparation (A) and a second compartment holding preparation (B). However, a multicompartment tube with more than two compartments, for example, three or four compartments, may also be used. In this case, preparation (A) and/or preparation (B) may be distributed between several compartments of the multicompartment tube although it is of course important to ensure that preparation (A) only or preparation (B) only is present in a particular compartment.

Two-compartment tubes are already known in principle in the prior art. In a particularly simple embodiment, the tubes have two separate compartments in the form of flexible tubes inserted into one another. These define the inner and the outer compartment and end in the common head or exit section. The head section is designed so that the two preparations issue from the tube together when pressure is applied to the tube. The design of the head section determines the stripe pattern in which the preparations issue from the tube. Known commercially available tubes have the same volume ratio of inner to outer tube and, hence, a mixing ratio of 50:50. The known tubes are unsuitable for products of which the two phases have to be separately stored and of which the mixing ratio differs from the standard ratio of 50:50.

The two-component compositions according to the invention are preferably made up in a two-compartment tube comprising an inner and an outer compartment both ending in a common head section (exit section). The head section is designed so that the two preparations issue from the tube together when pressure is applied to the tube. The design of the head section determines the pattern in which the preparations issue from the tube.

The choice of the volumes of the individual compartments is governed by the desired ratio by volume between preparation (A) and preparation (B) in the two-component composition.

The two-compartment tube preferably used is distinguished in particular by a particular design of the exit section where the ratio of the compartment volumes is reflected in the cross-sections of the paths defined for the component streams. It is pointed out in this regard that the stream of one preparation can have several parallel branch streams. Thus, parting agents can divide the cross-section of the through-flow passage into two or more component streams at least substantially in accordance with the ratio. It is pointed out in this connection that it is advantageous to the function of the two-compartment tubes if the various components present in the respective tube compartments have substantially the same viscosity.

Although, in principle, the invention is not intended in any way to be limited in regard to the pattern in which the preparations issue from the tube, it can be preferred in accordance with the invention for the first preparation to issue as the main strand and for the second preparation to form several stripes running along the main strand. The invention is also not limited in regard to the number of stripes. However, a number of two to four stripes can be particularly preferred for application reasons. In a first embodiment, preparation (A) can form the stripes while preparation (B) forms the main strand and, in a second embodiment, preparation (B) forms the stripes while preparation (A) forms the main strand.

In another preferred embodiment, however, the two preparations together can proportionately form the main strand alongside one another. In another embodiment, the exit strand may consist of an inner section formed from a first preparation and an outer section formed from the second preparation, the preparations also forming the exit strand according to their arrangement in the tube.

In a preferred embodiment of the invention, the quantity ratio between preparations (A) and (B) is in the range from 1:2 to 5:1, and more particularly, in the range from 1:1 to 3:1.

In principle, the present invention is intended to encompass any distribution of the compartments within the tube. In a first embodiment for example, the two individual compartments may be disposed beside one another in an outer envelope. In a particularly preferred embodiment of the invention, the two-compartment tube consists of an inner tube which is completely surrounded by an outer tube. This embodiment is distinguished by an optimally constant dosage of the two preparations. Although, in principle, any distribution of the preparations between the compartments of the tube is intended to be covered by the invention, a particularly preferred embodiment is characterized in that preparation (A) is accommodated in the outer tube and preparation (B) in the inner tube.

The two-compartment tube is preferably made of a material which is suitable for the packaging of tinting and coloring preparations of the type in question. According to the invention, laminated aluminium has proven to be particularly suitable both for the outer walls and for the inner walls. However, tubes of plastic laminate (PE, PET, PP) or plastic co-extrudates (PE, PET, PP) would also be suitable. In addition, in one embodiment, the material of the inner tube may be selected independently of the material of the outer tube.

A most particularly preferred embodiment of a tube according to the invention is characterized in that the inner tube is made of aluminium laminate optionally protected by a lacquer while the outer tube is made either of aluminium laminate or of plastic laminate. In the context of the invention, aluminium laminate is understood to be a layer of aluminium coated with plastic.

In a particularly advantageous embodiment, the shoulder region of the tube is reinforced by round blanks which have particularly good barrier properties. Aluminium is beneficially incorporated in the material of the round blanks.

In order to prevent the mixture from escaping in storage and to guarantee the consumer the integrity of the tube, the discharge opening is beneficially sealed with an initial seal of aluminium or plastic which is removed by the user.

Besides the components essential to the invention, preparations (A) and (B) may contain any of the active components, additives and auxiliaries known for such preparations.

In many cases, the colorants contain at least one surfactant. In principle, both anionic and zwitterionic, ampholytic, nonionic and cationic surfactants are suitable. In many cases, however, it has proven to be advantageous to select the surfactants from anionic, zwitterionic and nonionic surfactants.

Suitable anionic surfactants for the preparations according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear fatty acids containing 10 to 22 carbon atoms (soaps), ether carboxylic acids corresponding to the formula R—O—($CH_2$—$CH_2$O)$_x$—$CH_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O($CH_2$—$CH_2$O)$_x$—$SO_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 mol ethylene oxide and/or propylene oxide onto fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

Nonionic surfactants contain, for example, a polyol group, a polyalkylene glycol ether group or a combination of polyol and polyglycol ether groups as the hydrophilic group. Examples of such compounds are:

products of the addition of 2 to 30 mol ethylene oxide and/or 0 to 5 mol propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 mol ethylene oxide onto glycerol, $C_{8-22}$ alkyl mono- and oligoglycosides and ethoxylated analogs thereof and products of the addition of 5 to 60 mol ethylene oxide onto castor oil and hydrogenated castor oil.

Preferred nonionic surfactants are alkyl polyglycosides corresponding to the general formula $R^1$O-(Z)$_x$. These compounds are characterized by the following parameters.

The alkyl group $R^1$ contains 6 to 22 carbon atoms and may be both linear and branched. Primary linear and 2-methyl-branched aliphatic groups are preferred. Such alkyl groups are, for example, 1-octyl, 1-decyl, 1-lauryl, 1-myristyl, 1-cetyl and 1-stearyl. 1-Octyl, 1-decyl, 1-lauryl and 1-myristyl are particularly preferred. Where so-called "oxo alcohols" are used as starting materials, compounds with an odd number of carbon atoms in the alkyl chain predominate.

The alkyl polyglyosides suitable for use in accordance with the invention may, for example, contain only one particular alkyl group R1. However, such compounds are normally prepared from natural fats and oils or mineral oils. In this case, mixtures corresponding to the starting compounds, or corresponding to the particular working up of these compounds, are present as the alkyl groups $R^1$.

Particularly preferred alkyl polyglycosides are those in which $R^1$ consists essentially of $C_8$ and $C_{10}$ alkyl groups, essentially of $C_{12}$ and $C_{14}$ alkyl groups, essentially of $C_8$ to $C_{16}$ alkyl groups or essentially of $C_{12}$ to $C_{16}$ alkyl groups.

Any mono- or oligosaccharides may be used as the sugar unit Z. Sugars containing 5 or 6 carbon atoms and the corresponding oligosaccharides are normally used. Examples of such sugars are glucose, fructose, galactose, arabinose, ribose, xylose, lyxose, allose, altrose, mannose, gulose, idose, talose and sucrose. Preferred sugar units are glucose, fructose, galactose, arabinose and sucrose; glucose is particularly preferred.

The alkyl polyglycosides suitable for use in accordance with the invention contain on average 1.1 to 5 sugar units. Alkyl polyglycosides with x values of 1.1 to 1.6 are preferred. Alkyl oligoglycosides where x is 1.1 to 1.4 are most particularly preferred.

Besides acting as surfactants, the alkyl glycosides may also be used to improve the fixing of perfume components to the hair. Accordingly, in cases where the effect of the perfume oil on the hair is intended to last longer than the duration of the hair treatment, alkyl glycosides will preferably be used as another ingredient of the preparations according to the invention.

Alkoxylated homologs of the alkyl polyglycosides mentioned may also be used in accordance with the invention. These homologs may contain on average up to 10 ethylene oxide and/or propylene oxide units per alkyl glycoside unit.

Zwitterionic surfactants may also be used, particularly as co-surfactants. In the context of the invention, zwitterionic surfactants are surface-active compounds which contain at least one quaternary ammonium group and at least one —COO$^{(-)}$ or —SO3$^{(-)}$ group in the molecule. Particularly suitable zwitterionic surfactants are the so-called betaines, such as N-alkyl-N,N-dimethyl ammonium glycinates, for example, cocoalkyl dimethyl ammonium glycinate, N-acylaminopropyl-N,N-dimethyl ammonium glycinates, cocoacylaminopropyl dimethyl ammonium glycinate and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the INCI name of Cocamidopropyl Betaine.

Also suitable, particularly as co-surfactants, are ampholytic surfactants. Ampholytic surfactants are surface-active compounds which, in addition to a $C_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

According to the invention, the cationic surfactants used are particularly those of the quaternary ammonium compound, esterquat and amidoamine type.

Preferred quaternary ammonium compounds are ammonium halides, more particularly chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride and the imidazolium compounds known under the INCI names of Quaternium-27 and Quaternium-83. The long alkyl chains of the above-mentioned surfactants preferably contain 10 to 18 carbon atoms.

Esterquats are known substances which contain both at least one ester function and at least one quaternary ammonium group as structural element. Preferred esterquats are quaternized ester salts of fatty acids with triethanolamine, quaternized ester salts of fatty acids with diethanol alkylamines and quaternized ester salts of fatty acids with 1,2-dihydroxypropyl dialkylamines. Such products are marketed, for example, under the names of Stepantex®, Dehyquart® and Armocare®. The products Armocare® VGH-70, an N,N-bis-(2-palmitoyloxyethyl)-dimethyl ammonium chloride, and Dehyquart® F-75 and Dehyquart® AU-35 are examples of such esterquats.

The alkyl amidoamines are normally prepared by amidation of natural or synthetic fatty acids and fatty acid segments with dialkyl aminoamines. A compound from this group particularly suitable for the purposes of the invention is the stearamidopropyl dimethylamine obtainable under the name of Tegoamid® S 18.

Other cationic surfactants suitable for use in accordance with the invention are the quaternized protein hydrolyzates.

Also suitable for the purposes of the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

One example of a quaternary sugar derivative suitable for use as a cationic surfactant is the commercially available product Glucquat®100 (INCI name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be advantageous.

The colorants according to the invention may also contain other active substances, auxiliaries and additives such as, for example, nonionic polymers such as, for example, vinyl pyrrolidone/vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamide/dimethyldiallyl ammonium chloride copolymers, dimethylaminoethyl methacrylate/vinyl pyrrolidone copolymers quaternized with diethyl sulfate, vinyl pyrrolidone/imidazolinium methochloride copolymers and quaternized polyvinyl alcohol, zwitterionic and amphoteric polymers such as, for example, acrylamidopropyl/trimethyl ammonium chloride/acrylate copolymers and octyl acrylamide/methyl methacrylate/tertbutyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tertbutyl acrylamide terpolymers, thickeners, such as agar agar, guar gum, alginates, xanthan gum, gum arabic, karaya gum, locust bean gum, linseed gums, dextrans, cellulose derivatives, for example, methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as maleic acid and lactic acid, hair-conditioning compounds, such as phospholipids, for example, soya lecithin, egg lecithin and kephalins, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solvents and solubilizers, such as ethanol, isopropanol, ethylene glycol, propylene glycol, glycerol and diethylene glycol, fiber-restructuring agents, more particularly mono, di and oligosaccharides such as, for example, glucose, galactose, fructose and lactose, quaternized amines, such as methyl-1-alkylamidoethyl-2-alkylimidazolinium methosulfate, defoamers, such as silicones, dyes for coloring the preparation, antidandruff agents, such as piroctone olamine, zinc omadine and climbazol, UV filters, more particularly derivatized benzophenones, cinnamic acid derivatives and triazines, substances for adjusting the pH value, for example, typical acids, more particularly food-grade acids and bases, active substances, such as allantoin, pyrrolidone carboxylic acids and salts thereof and bisabolol, vitamins, provitamins and vitamin precursors, more particularly those of groups A, $B_3$, $B_5$, $B_6$, C, E, F and H, plant extracts, such as the extracts of green tea, oak bark, stinging nettle, hamamelis, hops, camomile, burdock root, horse willow, hawthorn, lime blossom, almond, aloe vera, pine needle, horse chestnut, sandalwood, juniper, coconut, mango, apricot, lemon, wheat, kiwi, melon, orange, grapefruit, sage, rosemary, birch, mallow, lady's smock, creeping thyme, yarrow, thyme, balm, restharrow, coltsfoot, hibiscus, meristem, ginseng and ginger root, cholesterol, consistency factors, such as sugar esters, polyol esters or polyol alkyl ethers, fats and waxes, such as spermaceti, beeswax, montan wax and paraffins, fatty acid alkanolamides, complexing agents, such as EDTA, NTA, β-alanine diacetic acid and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, styrene/PVP and styrene/acrylamide copolymers, pearlizers, such as ethylene glycol mono- and distearate and PEG-3-distearate, preservatives, stabilizers for hydrogen peroxide and other oxidizing agents, propellants, such as propane/butane mixtures, $N_2O$, dimethyl ether, $CO_2$ and air, antioxidants.

Information on other optional components and the quantities in which they are used can be found in the reference books known to the expert, for example, Kh. Schrader, Grundlagen und Rezepturen der Kosmetika, 2nd Edition, Hüthig Buch Verlag, Heidelberg, 1989.

According to the invention, preparations (A) and (B) contain the components essential to the invention preferably in a suitable aqueous, alcoholic or aqueous/alcoholic carrier. For coloring hair, such carriers are, for example, creams, emulsions, gels or even surfactant-containing foaming solutions such as, for example, shampoos, foam aerosols or other preparations suitable for application to the hair.

Aqueous/alcoholic solutions in the context of the invention are aqueous solutions containing 3 to 70% by weight of a $C_{1-4}$ alcohol, more particularly ethanol or isopropanol. The preparations according to the invention may additionally contain other organic solvents such as, for example, methoxybutanol, benzyl alcohol, ethyl diglycol or 1,2-propylene glycol. Water-soluble organic solvents are preferred.

The two-component compositions according to the invention may additionally contain a reducing agent. Examples of preferred reducing agents for the purposes of the invention are sodium sulfite, ascorbic acid, thioglycolic acid and derivatives thereof, sodium thionite, alkali metal citrate salts and N-acetyl-L-cysteine. Particularly preferred reducing agents are alkali metal citrate salts, more especially sodium citrate, and N-acetyl-L-cysteine. N-acetyl-L-cysteine is a most particularly preferred reducing agent.

The compositions according to the invention may additionally contain alkalizing agents, typically alkali metal or alkaline earth metal hydroxides, ammonia or organic amines. Preferred alkalizing agents are monoethanolamine, monoisopropanolamine, 2-amino-2-methylpropanol, 2-amino-2-methylpropane-1,3-diol, 2-amino-2-ethylpropane-1,3-diol, 2-amino-2-methylbutanol and triethanolamine and alkali metal and alkaline earth metal hydroxides. Within this group, monoethanolamine, triethanolamine and 2-amino-2-methylpropanol and 2-amino-2-methylpropane-1,3-diol are particularly preferred. ω-Amino acids, such as ω-aminocaproic acid, may also be used as the alkalizing agent.

Pearl luster pigments are often used for this purpose. Pearl luster pigments preferred for the purposes of the invention are natural pearl luster pigments such as, for example, pearl essence (guanine/hypoxanthine mixed crystals from fish scales) or mother of pearl (from ground-up mussel shells), monocrystalline pearl luster pigments, such as bismuth oxychloride, for example, and pearl luster pigments based on mica or mica/metal oxide. The last of the above-mentioned pearl luster pigments are provided with a metal oxide coating. By using the pearl luster pigments, luster and, optionally, color effects are obtained in the two-component compositions according to the invention. However, the color effect of the pearl luster pigments used in the two-component compositions does not influence the outcome of the coloring of the keratin fibers.

Pearl luster pigments based on mica and on mica/metal oxide are also preferred for the purposes of the invention. Mica is one of the layer silicates. The most important representatives of these silicates are muscovite, phlogopite, paragonite, biotite, lepidolite and margarite. To produce the pearl luster pigments in conjunction with metal oxides, the mica—predominantly muscovite or phlogopite—is coated with a metal oxide. Suitable metal oxides are, inter alia, $TiO_2$, $Cr_2O_3$ and $Fe_2O_3$. Appropriate coating results in interference pigments and color luster pigments as pearl luster pigments according to the invention. Besides a glittering visual effect, these types of pearl luster pigment also have color effects. In addition, the pearl luster pigments usable in accordance with the invention may also contain a color pigment that is not derived from a metal oxide.

The particle size of the pearl luster pigments preferably used is preferably between 1.0 and 100 μm, and more particularly, between 5.0 and 60.0 μm.

Particularly preferred pearl luster pigments are pigments marketed by Merck under the name of Colorona®, the pigments Colorona® red-brown (47-57% by weight muscovite mica ($KH_2(AlSiO_4)_3$), 43-50% by weight $Fe_2O_3$ (INCI: Iron Oxides CI 77491), <3% by weight $TiO_2$ (INCI: Titanium Dioxide CI 77891), Colorona® Blackstar Blue (3947% by weight muscovite mica ($KH_2(AlSiO_4)_3$), 53-61% by weight $Fe_3O_4$ (INCI: Iron Oxides CI 77499)), Colorona® Siena Fine (35-45% by weight muscovite mica ($KH_2(AlSiO_4)_3$), 55-65% by weight $Fe_2O_3$ (INCI: Iron Oxides CI 77491)), Colorona® Aborigine Amber (50-62% by weight muscovite mica ($KH_2(AlSiO_4)_3$), 36-44% by weight $Fe_3O_4$ (INCI: Iron Oxides CI 77499), 2-6% by weight $TiO_2$ (INCI: Titanium-Dioxide CI 77891)), Colorona® Patagonian Purple (42-54% by weight muscovite mica ($KH_2(AlSiO_4)_3$), 26-32% by weight $Fe_2O_3$ (INCI: Iron Oxides CI 77491), 18-22% by weight $TiO_2$ (INCI: Titanium Dioxide CI 77891), 2-4% by weight Prussian Blue (INCI: Ferric Ferrocyanide CI 77510)), Colorona® Chameleon (40-50% by weight muscovite mica ($KH_2(AlSiO_4)_3$), 50-60% by weight $Fe_2O_3$ (INCI: Iron Oxides CI 77491)) and Silk® Mica (>98% by weight muscovite mica ($KH_2(AlSiO_4)_3$)) being most particularly preferred.

With regard to the pearl luster pigments suitable for use in the two-component compositions according to the invention, reference is expressly made to the monographs Inorganic Pigments, Chemical Technology Review No. 166, 1980, pages 161-173 (ISBN 0-8155-0811-5) and Industrial Inorganic Pigments, 2nd Edition, Weinheim, VCH, 1998, pages 211-231.

In principle, the actual oxidative coloring of the fibers may be carried out with atmospheric oxygen. However, a chemical oxidizing agent is preferably used, particularly when human hair is not only to be colored, but also lightened. Particularly suitable oxidizing agents are persulfates, chlorites and, in particular, hydrogen peroxide or addition products thereof with urea, melamine or sodium borate. According to the invention, however, the oxidation colorant may also be applied to the hair together with a catalyst which activates the oxidation of the dye precursors, for example, by atmospheric oxygen. Such catalysts are, for example, metal ions, iodides, quinones or certain enzymes.

Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. $Zn^{2+}$, $Cu^{2+}$ and $Mn^{2+}$ are particularly suitable. Basically, the metal ions may be used in the form of a physiologically compatible salt or in the form of a complex compound. Preferred salts are the acetates, sulfates, halides, lactates and tartrates. Development of the hair color can be accelerated and the color tone can be influenced as required through the use of these metal salts.

Suitable enzymes are, for example, peroxidases which are capable of significantly enhancing the effect of small quantities of hydrogen peroxide. According to the invention, other suitable enzymes are those which directly oxidize the oxidation dye precursors with the aid of atmospheric oxygen, such as the laccases, for example, or which produce small quantities of hydrogen peroxide in situ and thus biocatalytically activate the oxidation of the dye precursors. Particularly suitable catalysts for the oxidation of the dye precursors are the so-called 2-electron oxidoreductases in combination with the substrates specific to them, for example:

- pyranose oxidase and, for example, D-glucose or galactose,
- glucose oxidase and D-glucose,
- glycerol oxidase and glycerol,
- pyruvate oxidase and pyruvic acid or salts thereof,
- alcohol oxidase and alcohol (MeOH, EtOH),
- lactate oxidase and lactic acid and salts thereof,
- tyrosinase oxidase and tyrosine,
- uricase and uric acid or salts thereof,
- choline oxidase and choline,
- amino acid oxidase and amino acids.

The actual hair colorant is preferably prepared immediately before application by mixing the preparation of the oxidizing agent with preparations (A) and (B) squeezed from the tube. The ready-to-use hair coloring preparation formed should preferably have a pH value in the range from 6 to 12. Unless otherwise stated, pH values mentioned in the present disclosure are values as measured at 25° C. In a particularly preferred embodiment, the hair colorant is used in an alkaline medium. The application temperatures may be in the range from 15 to 40° C. After a contact time of about 5 to 45 minutes, the hair colorant is removed from the hair to be colored by rinsing. There is no need for the hair to be washed with a shampoo where a carrier of high surfactant content, for example, a coloring shampoo, has been used.

However, in the particular case of hair which is difficult to color, the two-component composition may be applied to the hair without preliminary mixing with the oxidation component. The oxidation component is applied after a contact time of 20 to 30 minutes, optionally after rinsing. After another contact time of 10 to 20 minutes, the hair is rinsed and, if desired, shampooed. In a first variant of this embodiment where the preliminary application of the dye precursors is intended to improve penetration into the hair, the corresponding formulation is adjusted to a pH value of about 4 to 7. In a second variant, oxidation with air is initially carried out, the formulation applied preferably having a pH value of 7 to 10. In the subsequent accelerated post-oxidation phase, it can be advantageous to use acidified peroxydisulfate solutions as the oxidizing agent.

Preparations (A) and (B) of the two-component composition according to the invention preferably have viscosities in the range from 2,000 to 200,000 mPas and more particularly in the range from 5,000 to 50,000 mPas (Brookfield viscosimeter, spindle No. 4, 20 r.p.m., 20° C.). This ensures that the two-component composition shows good miscibility while the exit pattern shows sufficient stability.

The present invention also relates to a process for coloring keratinous fibers, more particularly, human hair, in which a two-component composition according to the invention is squeezed from the tube, mixed with an oxidizing agent preparation, the resulting preparation is applied to the fibers and, after a contact time, is rinsed off again.

The following Examples are intended to illustrate the invention without limiting it in any way.

EXAMPLES

The following formulations were prepared. The figures shown represent quantities in % by weight.

Formulations for Preparation (A).

| Raw materials | Coloring cream | | | | | |
| --- | --- | --- | --- | --- | --- | --- |
| | A | B | C | D | E | F |
| Texapon ® K14 S 70 C | 2.8 | 2.8 | 2.8 | 2.8 | 2.8 | 2.8 |
| Phopholipid ® EFA | 1.0 | — | — | 1.0 | — | — |
| Plantacare ® 1200 UP | 2.0 | 2.0 | — | — | — | — |
| Lamesoft ® PO65 | — | — | — | 2.0 | 2.0 | — |
| Akypo Soft ® 45 NV | 10.0 | 8.0 | 10.0 | 10.0 | 8.0 | 10.0 |
| Hydrenol ® D | 8.0 | 8.0 | 8.0 | 8.0 | 8.0 | 8.0 |
| Kokoslorol ® | 2.0 | 2.0 | 2.0 | 2.0 | 2.0 | 2.0 |
| Eutanol ® G | 1.0 | 1.5 | 1.0 | 1.0 | 1.5 | 1.0 |
| Eumulgin ® B1 | 0.5 | 0.5 | 0.5 | 0.5 | 0.5 | 0.5 |
| Eumulgin ® B2 | 0.5 | 0.5 | 0.5 | 0.5 | 0.5 | 0.5 |
| KOH, 50% | 0.7 | 1.0 | 2.0 | 0.7 | 1.0 | 2.0 |
| Coloring powder mixture | a | b | c | a | b | c |
| Water, deionized | to 100 | to 100 | to 100 | to 100 | to 100 | to 100 |
| Ascorbic acid | 0.1 | 0.05 | 0.1 | 0.1 | 0.05 | 0.1 |
| Sodium sulfite | 0.15 | 0.2 | 0.3 | 0.1 | 0.2 | 0.3 |
| Ammonia, 25% | 6.0 | 8.0 | 6.0 | 6.0 | 8.0 | 6.0 |
| Turpinal ® SL | 0.2 | 0.2 | 0.2 | 0.2 | 0.2 | 0.2 |
| Mirapol ® A 15 | 0.2 | — | 0.2 | 0.2 | — | 0.2 |
| Perfume | 0.25 | 0.25 | 0.25 | 0.25 | 0.25 | 0.25 |

| Raw materials | Coloring cream | | |
| --- | --- | --- | --- |
| | G | H | I |
| Texapon ® NSO | 7.0 | 7.0 | 7.0 |
| Dehyton ® K | 5.0 | 5.0 | 5.0 |
| Prisorine ® 3501 | 2.0 | 2.0 | 2.0 |
| Edenor ® C14 | 0.5 | 0.5 | 0.5 |
| Phospholipid EFA | 1.0 | 1.0 | — |
| Plantacare ® 1200 UP | 0.5 | — | 0.5 |
| Hydrenol ® D | 8.0 | 8.0 | 8.0 |
| Kokoslorol ® | 2.5 | 2.5 | 2.5 |
| Eumulgin ® B1 | 0.5 | 0.5 | 0.5 |
| Eumulgin ® B2 | 0.5 | 0.5 | 0.5 |
| KOH, 50% | 0.7 | 1.0 | 2.0 |

-continued

| Raw materials | Coloring cream | | |
|---|---|---|---|
| | G | H | I |
| Coloring powder mixture | a | b | c |
| Water, deionized | to 100 | to 100 | to 100 |
| Sodium sulfite | 0.15 | 0.2 | 0.3 |
| Ascorbic acid | 0.1 | 0.05 | 0.1 |
| Ammonia, 25% | 6.0 | 8.0 | 6.0 |
| Turpinal ® SL | 0.2 | 0.2 | 0.2 |
| Mirapol ® A 15 | 0.2 | — | — |
| Parfum | 0.3 | 0.3 | 0.3 |

Parfum 0.3 0.3 0.3

The following coloring powder mixtures a, b and c were used in coloring creams A to I:

| Raw material | Coloring powder mixture a |
|---|---|
| p-Toluylenediamine sulfate | 0.90 |
| Resorcinol | 0.20 |
| m-Aminophenol | 0.06 |
| 4-Chlororesorcinol | 0.15 |
| Color | Blond |

| Raw material | Coloring powder mixture b |
|---|---|
| p-Toluylene diamine sulfate | 0.20 |
| 1-(2-Hydroxyethyl)-4,5-diaminopyrazole | 1.50 |
| m-Aminophenol | 0.05 |
| 5-Amino-2-methylphenol | 0.80 |
| Color | Red |

| Raw material: | Coloring powder mixture c |
|---|---|
| p-Toluylene diamine sulfate | 2.20 |
| Resorcinol | 0.30 |
| 2,4-Diaminophenoxyethanol hydrochloride | 1.70 |
| Color | Blue-black |

Formulations for Preparation (B).

| Raw material | Care component B1 |
|---|---|
| Cetylstearyl alcohol | 8.0 |
| Eumulgin ® B1 | 2.0 |
| Dehyquart ® A-CA | 1.0 |
| Merquat ® 100 | 0.5 |
| Paraffin oil DAB 7 | 0.3 |
| Phenoxyethanol | 0.8 |
| Panthenol | 2.0 |
| Sodium benzoate | 0.04 |
| Promois ® Silk 1000 | 0.5 |
| Mica | 0.1 |
| Citric acid | to pH 6.5 |
| Water dist. | to 100 |

| Raw material | Care component B2 |
|---|---|
| Stearyl stearate | 2.00 |
| Cetyl alcohol | 6.00 |
| Ceteth-20 | 4.00 |
| Propylene glycol | 1.00 |
| Polymer ® W 37194 | 0.75 |
| Vitamin $B_6$ | 1.0 |
| Phenoxyethanol | 0.9 |
| Sodium benzoate | 0.5 |
| Sodium salicylate | 0.4 |
| Phosphoric acid | to pH 6 |
| Perfume | 0.3 |
| Water | to 100 |

| Raw material | Care component B3 |
|---|---|
| Texapon ® K14 S 70 C | 2.8 |
| Phopholipid ® EFA | 1.0 |
| Lamesoft ® PO65 | 2.0 |
| Akypo Soft ® 45 NV | 10.0 |
| Hydrenol ® D | 8.0 |
| Kokoslorol ® | 2.0 |
| Eutanol ® G | 1.0 |
| Eumulgin ® B1 | 0.5 |
| Eumulgin ® B2 | 0.5 |
| Vitamin $B_6$ | 0.5 |
| Mica | 0.1 |
| Polymer ® W 37194 | 0.75 |
| 2-Amino-2-methylpropanol | to pH 9 |
| Mirapol ® A 15 | 0.2 |
| Perfume | 0.25 |
| Water | to 100 |

| Raw material | Care component B4 |
|---|---|
| Texapon ® NSO | 7.0 |
| Dehyton ® K | 5.0 |
| Prisorine ® 3501 | 2.0 |
| Edenor ® C14 | 0.5 |
| Hydrenol ® D | 8.0 |
| Kokoslorol ® | 2.5 |
| Eumulgin ® B1 | 0.5 |
| Eumulgin ® B2 | 0.5 |
| Glucose monohydrate | 0.15 |
| Glyceric acid | 0.1 |
| Mirapol ® A 15 | 0.2 |
| Monoethanolamine | to pH 8 |
| Water, deionized | to pH 100 |

Formulation for the Oxidizing Agent Preparation

| Raw material | Oxidizing agent preparation |
| --- | --- |
| Dipicolinic acid | 0.1% by weight |
| Sodium pyrophosphate | 0.03% by weight |
| Turpinal ® SL | 1.50% by weight |
| Texapon ® N28 | 2.00% by weight |
| Acrysol ® 22 | 0.60% by weight |
| Hydorgen peroxide, 50% | 12.00% by weight |
| Sodium hydroxide, 45% | 0.80% by weight |
| Water | to 100% by weight |

Coloring.

Coloring creams A to I were made up in a ratio of 3:1 with care components B1 and B2 or in a ratio of 1:1 with care components B3 and B4 in a two-compartment tube. Immediately before application, the two-component composition was squeezed from the two-compartment tube into an application bowl, in which it was mixed with the oxidizing agent preparation mentioned above. The resulting preparation was then applied to human hair (Kerling natural white), rubbed in, left to act for 30 minutes and then rinsed out. Intensive blond, red or blue-black colors were obtained after drying of the hair.

Index of Commercial Products Used.

The commercial products used in the Examples are defined in the following:

| | |
| --- | --- |
| Acrysol ® 22 | Acrylic polymer (ca. 29.5-30.5% solids in water; INCI name: Acrylates/Steareth-20 Methacrylate Copolymer) |
| Akypo Soft 45 NV ® | Laurylalkohol-4.5-EO-acetic acid sodium salt (at least 21% active substance content; INCI name: Sodium Laureth-6 Carboxylate) (Chem-Y) |
| Dehyquart ® A-CA | Trimethylhexadecyl ammonium chloride (ca. 24-26% active substance; INCI name: Aqua (Water), Cetrimonium Chloride) (Cognis) |
| Dehyton ® K | N,N-Dimethyl-N-($C_{8-18}$-cocoamido-propyl)ammonium acetobetaine (30% active substance; INCI name: Aqua (Water), Cocamidopropyl Betaine) (Cognis) |
| Edenor ® C14 | Myristic acid (INCI name: MYRISTIC ACID) (Cognis) |
| Eumulgin ® B 1 | Cetylstearyl alcohol containing ca. 12 EO units (INCI Bezeichnung: Ceteareth-12) (Cognis) |
| Eumulgin ® B2 | Cetylstearyl alcohol containing ca. 20 EO units (INCI name: Ceteareth-20) (Cognis) |
| Eutanol ® G | 2-Octyldodecyl alcohol (INCI name: Octyldodecanol) (Cognis) |
| Hydrenol ® D | $C_{16-18}$ Fatty alcohol (INCI name: Cetearyl alcohol) (Cognis) |
| Kokoslorol ® | $C_{12-18}$ fatty alcohol (INCI-Bezeichnung: Coconut Alcohol) (Cognis) |
| Lamesoft ® PO65 | Alkyl polyglucoside/oleic acid monoglyceride mixture (ca. 65-70% solids content; INCI name: Coco-Glucoside, Glyceryl Oleate, Aqua (Water)) (Cognis) |
| Merquat ® 100 | Poly(dimethyldiallylammoniumchloride) (ca. 40% solids content; INCI name: Polyquaternium-6) (Ondeo Nalco) |
| Mirapol ® A 15 | Poly[N-(3-(dimethylammonium)propyl]-N'-[3-ethyleneoxy-ethylenedimethylammonium)-propyl]-urea dichloride (ca. 64% solids content in water; INCI name: Polyquaternium-2) (Rhodia) |
| Phopholipid ® EFA | (INCI name: Linoleamidopropyl PG-Dimonium Chloride Phosphate) (Unichema) |
| Plantacare ® 1200 UP | $C_{12-16}$ fatty alcohol-1,4-glucoside (ca. 50-53% active substance content; INCI-Bezeichnung: Lauryl Glucoside, Aqua (Water)) (Cognis) |
| Polymer ® W 37194 | ca. 20% by weight active substance content in water; INCI name: Acrylamidopropyltrimonium Chloride/Acrylates Copolymer (Stockhausen) |
| Prisorine ® 3501 | Isooctadecanoic acid (INCI name: Isostearic Acid) (Unichema) |
| Promois Silk ® 1000 | Collagen Hydrolyzate (ca. 5-8% solids content; INCI name: HYDROLYZED SILK) (Interorgana) |
| Texapon ® K 14 S 70 | C Lauryl myristylether sulfate sodium salt (ca. 68% to 73% active substance content; INCI name: Sodium Myreth Sulfate) (Cognis) |
| Texapon ® N28 | Laurylether sulfate sodium salt (at least 26.5% active substance content; INCI name: Sodium Laureth Sulfate) (Cognis) |
| Texapon ® NSO | Laurylether sulfate, sodium salt (ca. 27.5% active substance; INCI name: Sodium Laureth Sulfate) (Cognis) |
| Turpinal ® SL | 1-Hydroxyethane-1,1-diphosphonic acid (ca. 58-61% active substance content; INCI name: Etidronic Acid, Aqua (Water)) (Solutia) |

The invention claimed is:

1. A two-component composition for coloring keratinous fibers comprising a first preparation (A) comprising at least one oxidation dye precursor and a second preparation (B) comprising at least one care component, wherein the first and second preparations are packaged separately from one another in the compartments of a two-chamber tube having an inner and outer chamber and a common exit region wherein the exit region is configured in such a way that said first preparation (A) exits as the main strand and said second preparation (B) forms a plurality of stripes running along the main strand or said second preparation (B) exits as the main strand and said first preparation (A) forms a plurality of stripes running along the main strand when pressure is exerted on the tube and wherein the ratio of preparation (A) to preparation (B) is in the range of from 1/2 to 5/1.

2. The composition of claim 1 wherein preparation (A) is comprised of at least one primary intermediate.

3. The composition of claim 1 wherein preparation (A) is comprised of at least one secondary intermediate.

4. The composition of claim 1 wherein preparation (A) further comprises at least one precursor of a nature-analogous dye.

5. The composition of claim 1 wherein preparation (A) further comprises at least one substantive dye.

6. The composition of claim 1 wherein preparation (B) further comprises at least one cationic surfactant.

7. The composition of claim 1 wherein preparation (B) further comprises at least one hair-care polymer.

8. The composition of claim 1 wherein preparation (B) further comprises at least one UV filter.

9. The composition of claim 1 wherein preparation (B) further comprises at least one vitamin, provitamin, vitamin precursor and/or derivative thereof.

10. The composition of claim 1 wherein preparation (B) further comprises at least one plant extract.

11. The composition of claim 1 wherein preparation (B) further comprises at least one protein hydrolyzate and/or derivative thereof.

12. The composition of claim 1 wherein preparation (B) further comprises at least one compound selected from the group consisting of ectoin or ectoin derivatives, allantoin, taurine and bisabolol.

13. The composition of claim 1 wherein preparation (B) further comprises at least one mono- or oligosaccharide.

14. The composition of claim 1 wherein preparation (B) further comprises at least one silicone oil and/or a silicone gum.

15. The composition of claim 1 wherein preparation (B) further comprises at least one oil component.

16. A two-compartment tube comprising a first compartment comprising a preparation (A) comprising at least one oxidation dye precursor and a second compartment comprising a preparation (B) comprising at least one care component wherein the compartment openings are oriented in such a way that the contents of each of the first and second compartments is emitted simultaneously into a common space wherein the first and second preparations are packaged separately in a two chamber tube having an inner and outer chamber and a common exit region wherein the exit region is configured in such a way that the first preparation exits as the main strand and the second preparation forms a plurality of stripes running along the main strand as soon as pressure is exerted on the tube and wherein the ratio of the chamber volumes is the same as the cross sections of the routes defined for the part-streams.

17. The tube of claim 16 wherein the preparations are emitted from the tube at a volume ratio of (A) to (B) corresponding to 1:1 to 1:3.

18. The tube of claim 16 wherein the preparations are emitted from the tube in a stripe-like pattern.

19. A method for coloring keratinic fibers in particular human hair comprising forming a first mixture comprised of preparations (A) and (B) by combining the preparations as they are emitted from the tube of claim 16, (2) forming a second mixture by combining the first mixture with an oxidizing agent; contacting keratinic fibers with the second mixture for a period of time and then removing the preparations from the fibers.

* * * * *